(12) United States Patent
Brooks et al.

(10) Patent No.: US 12,147,228 B2
(45) Date of Patent: Nov. 19, 2024

(54) DISTRIBUTED VEHICLE SYSTEM CONTROL SYSTEM AND METHOD

(71) Applicant: Transportation IP Holdings, LLC, Norwalk, CT (US)

(72) Inventors: James D Brooks, Schenectady, NY (US); Harry Kirk Mathews, Jr., Niskayuna, NY (US); Paul Houpt, Niskayuna, NY (US)

(73) Assignee: Transportation IP Holdings, LLC, Norwalk, CT (US)

( * ) Notice: Subject to any disclaimer, the term of this patent is extended or adjusted under 35 U.S.C. 154(b) by 550 days.

(21) Appl. No.: 16/885,318

(22) Filed: May 28, 2020

(65) Prior Publication Data

US 2020/0363797 A1 Nov. 19, 2020

Related U.S. Application Data

(63) Continuation of application No. 15/460,431, filed on Mar. 16, 2017, now Pat. No. 10,705,519.
(Continued)

(51) Int. Cl.
*G05D 1/00* (2024.01)
*A61B 5/00* (2006.01)
(Continued)

(52) U.S. Cl.
CPC ......... *G05D 1/0027* (2013.01); *A61B 5/0077* (2013.01); *A61B 5/0205* (2013.01);
(Continued)

(58) Field of Classification Search
CPC ....... A61B 5/369; A61B 5/318; A61B 5/0077; A61B 5/0205; A61B 5/11; A61B 5/18;
(Continued)

(56) References Cited

U.S. PATENT DOCUMENTS

| 5,448,479 A | 9/1995 | Kemner et al. |
| 6,837,466 B2 | 1/2005 | Peltz |

(Continued)

FOREIGN PATENT DOCUMENTS

| AU | 2015205877 A1 | 8/2015 |
| EP | 2455270 | 5/2012 |

(Continued)

OTHER PUBLICATIONS

First Examination Report for AU Application No. 2017202698 dated Dec. 9, 2019.
(Continued)

*Primary Examiner* — Peter D Nolan
*Assistant Examiner* — Luke Huynh
(74) *Attorney, Agent, or Firm* — K&L Gates LLP

(57) ABSTRACT

A distributed control system includes a remote control system configured to be communicatively coupled with plural separate vehicle systems. The remote control system is configured to remotely control operation of the vehicle systems and/or communicate with the local vehicle control system or operator. The remote control system also is configured to one or more of change how many of the vehicle systems are concurrently controlled by the remote control system or change how many remote operators of the remote control system concurrently control the same vehicle system of the vehicle systems.

20 Claims, 12 Drawing Sheets

Related U.S. Application Data

(60) Provisional application No. 62/327,101, filed on Apr. 25, 2016.

(51) Int. Cl.
| | |
|---|---|
| *A61B 5/0205* | (2006.01) |
| *A61B 5/11* | (2006.01) |
| *A61B 5/18* | (2006.01) |
| *A61B 5/318* | (2021.01) |
| *A61B 5/369* | (2021.01) |
| *B61L 27/14* | (2022.01) |
| *B61L 27/40* | (2022.01) |
| *A61B 5/021* | (2006.01) |
| *A61B 5/024* | (2006.01) |
| *A61B 5/08* | (2006.01) |
| *B61L 3/12* | (2006.01) |
| *G06Q 10/0631* | (2023.01) |
| *G06Q 50/40* | (2024.01) |
| *G08G 9/00* | (2006.01) |
| *H04L 67/12* | (2022.01) |
| *H04L 67/52* | (2022.01) |

(52) U.S. Cl.
CPC ............ *A61B 5/11* (2013.01); *A61B 5/18* (2013.01); *A61B 5/318* (2021.01); *A61B 5/369* (2021.01); *B61L 27/14* (2022.01); *B61L 27/40* (2022.01); *G05D 1/0077* (2013.01); *A61B 5/021* (2013.01); *A61B 5/024* (2013.01); *A61B 5/0816* (2013.01); *B61L 3/127* (2013.01); *G05D 1/0016* (2013.01); *G06Q 10/0631* (2013.01); *G06Q 50/40* (2024.01); *G08G 9/00* (2013.01); *H04L 67/12* (2013.01); *H04L 67/52* (2022.05)

(58) Field of Classification Search
CPC ....... B61L 27/14; B61L 27/40; G05D 1/0027; G05D 1/0077
USPC .......................................................... 701/2
See application file for complete search history.

(56) References Cited

U.S. PATENT DOCUMENTS

| | | |
|---|---|---|
| 7,520,472 B2 | 4/2009 | Peltz et al. |
| 7,711,842 B2 | 5/2010 | Liu et al. |
| 8,050,809 B2 | 11/2011 | Geiger et al. |
| 8,401,720 B2 | 3/2013 | Daum et al. |
| 8,532,842 B2 | 9/2013 | Smith et al. |
| 8,676,410 B2 | 3/2014 | Houpt et al. |
| 9,110,468 B2 | 8/2015 | Funke et al. |
| 2004/0209594 A1* | 10/2004 | Naboulsi ............. H04M 1/6083 455/403 |
| 2004/0245410 A1* | 12/2004 | Kisak ...................... B61L 27/20 246/3 |
| 2005/0143874 A1 | 6/2005 | Peltz et al. |
| 2013/0018531 A1* | 1/2013 | Kumar ................ B61L 15/0027 701/2 |
| 2014/0188306 A1 | 7/2014 | Kumar et al. |
| 2014/0249699 A1* | 9/2014 | Cooper .................. B60L 15/32 701/2 |
| 2015/0037576 A1 | 2/2015 | Kataoka et al. |
| 2015/0248131 A1 | 9/2015 | Farfield et al. |
| 2016/0194014 A1 | 7/2016 | Rajendran |
| 2020/0363797 A1 | 11/2020 | Brooks et al. |

FOREIGN PATENT DOCUMENTS

| | | |
|---|---|---|
| EP | 2481653 B1 | 3/2014 |
| JP | 5506423 B2 | 5/2014 |
| WO | 2012095658 A1 | 7/2012 |

OTHER PUBLICATIONS

Coombes Ian, Developing Applications Using Locomotive Remote Control System Creates Rail Transport Solutions, Conference on Railway Engineering Proceedings: Engineering Innovation for a Competitive Edge, pp. 261-264; 1998.

* cited by examiner

DISTRIBUTED VEHICLE SYSTEM CONTROL SYSTEM AND METHOD

CROSS-REFERENCE TO RELATED APPLICATIONS

This application is a continuation of U.S. patent application Ser. No. 15/460,431, which was filed on 16 Mar. 2017, which claims priority to U.S. Provisional Application No. 62/327,101, which was filed on 25 Apr. 2016. The entire disclosures of which are incorporated herein by reference.

FIELD

The subject matter described herein relates to control systems and methods for vehicle systems.

BACKGROUND

Vehicle systems may be controlled by onboard and/or off-board operators. For example, rail vehicles (e.g., trains), automobiles, trucks, marine vessels, etc., may have persons onboard the vehicles in order to control operations such as throttle positions, brake applications, etc. In complex vehicle systems, several operators may be onboard to monitor and control operations of the vehicle systems. One operator may control throttle and brake systems while one or more other operators monitor other aspects of the vehicle systems, such as watching for obstructions along a direction of travel of the vehicle systems, monitoring the vehicle systems for unsafe operations, handling other mission planning activities and paperwork, etc.

One problem with having multiple operators onboard the same vehicle system is that the operators are limited to being on, and working on, the single vehicle system. An operator onboard one vehicle system is unable to control operation of another, separate and different vehicle system. For the operator to control one or more operations of another vehicle system, the vehicle system that the operator is currently on must stop to allow the operator to leave the current vehicle system and board another vehicle system in order to control operations of the other vehicle system. The operator is not able to concurrently control operations of multiple vehicle systems.

Off-board operation of some vehicle systems can include an operator disposed outside of the vehicle system with a remove control device. For example, an operator may have an operator control unit (OCU) and be located along the route on which the vehicle system is traveling or in a tower elevated above the vehicle system may remotely control the throttle of the vehicle system. But, the operator's remote control of the vehicle system is limited by the wireless communication range of the OCU and visual range of the operator, both of which can be limited to a mile (e.g., 1.6 kilometers) or less. Additionally, the OCU typically is communicatively linked with a single vehicle system to avoid the OCU inadvertently controlling another vehicle system. Consequently, the operator is limited to remotely controlling a single vehicle system over a relatively small and limited range.

BRIEF DESCRIPTION

In one embodiment, a distributed control system includes a remote control system configured to be communicatively coupled with plural separate vehicle systems. The remote control system is configured to remotely control operation of the vehicle systems and/or communicate with the local vehicle control system or operator. The remote control system also is configured to one or more of change how many of the vehicle systems are concurrently controlled by the remote control system or change how many remote operators of the remote control system concurrently control the same vehicle system of the vehicle systems.

In one embodiment, a method includes communicatively coupling a remote control system with plural separate vehicle systems, generating control inputs from the remote control system to remotely control operation of the vehicle systems, and one or more of changing how many of the vehicle systems are concurrently controlled by the remote control system or changing how many remote operators of the remote control system concurrently control the same vehicle system of the vehicle systems.

In one embodiment, a distributed control system includes a vehicle control system configured to be disposed onboard a vehicle system formed from one or more vehicles. The vehicle control system is configured to control movement of the vehicle system. The distributed control system also includes a remote control system configured to be communicatively coupled with the vehicle control system. The remote control system is configured to communicate control inputs from one or more off-board operators of the remote control system to the vehicle system in order to remotely control the movement of the vehicle system. The remote control system is configured to change how many of the off-board operators concurrently generate the control inputs for communication from the remote control system to the vehicle control system for remote control of the vehicle system.

In one embodiment, a vehicle control system includes a controller configured to be disposed onboard a vehicle system and to be communicatively coupled with one or more of a propulsion system or a braking system of the vehicle system. The controller is configured to receive operational set points designated by an operator located onboard the vehicle system and to determine operational settings of the one or more of the propulsion system or the braking system that drives the vehicle system to move according to the operational set points designated by the operator.

BRIEF DESCRIPTION OF THE DRAWINGS

The present inventive subject matter will be better understood from reading the following description of non-limiting embodiments, with reference to the attached drawings, wherein below.

DETAILED DESCRIPTION

Figure 1:
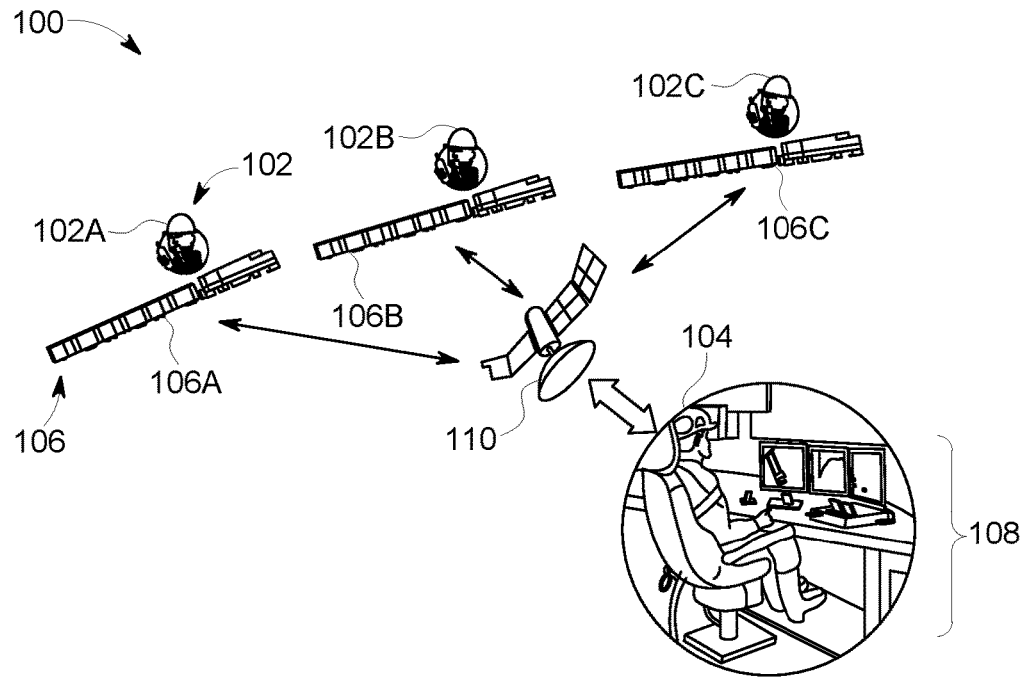
FIG. 1 illustrates one embodiment of a distributed control system.

FIG. 1 illustrates one embodiment of a distributed control system 100. The distributed control system is distributed such that multiple operators 102 (e.g., 102A-C), 104 located in multiple, different, and remote locations are able to work on, control operations, and/or monitor operations of multiple, separate vehicle systems 106 (e.g., 106A-C). The operators 102, 104 may be in remote locations when at least one of the operators is off-board the vehicle system being controlled, with these operators concurrently controlling operations of the same vehicle system. For example, the operator 102A may be located onboard the vehicle system 102A to locally control operations of the vehicle system 102A and the operator 104 may be located off-board the vehicle system 102A to control one or more of the same or different operations of the same vehicle system 102A. The vehicle systems may be separate when the vehicle systems are not mechanically coupled with each other and are not traveling with each other. The vehicle systems described herein may include a variety of different types of vehicles. For example, the vehicle systems may include rail vehicle systems (e.g., trains), automobiles, marine vessels, aircraft (e.g., drones), etc. and may be manned by one or more operators or be unmanned (i.e., more autonomous). While the vehicle systems are illustrated as trains, not all embodiments may be limited to trains. The vehicle systems are not model or toy vehicles in at least one embodiment of the subject matter described herein.

In one embodiment, the distributed control system includes a highly automated vehicle control system (not shown in FIG. 1) which is optionally manned by at least one operator 102 disposed onboard the vehicle system (also referred to as a local or onboard crew member) and a remote control system or station 108 that supports another operator 104 (also referred to as a remote or off-board crew member. Alternatively, the vehicle system may be controlled by the remote and local control systems without any human operator disposed onboard the vehicle system. The remote crew member may use the remote station to control the operations of multiple vehicle systems. For example, the remote crew member may use the remote station to switch between controlling operations of different vehicle systems 102A-C at different times and/or controlling operations of two or more vehicle systems 102A-C at the same time.

The vehicle and remote control systems are communicatively coupled by one or more networks. These networks can be wireless networks, such as networks that communicate signals between wireless communication devices 110, such as antennas, satellites, routers, etc. The remote crew member or operator may monitor and/or control operations of the vehicle systems via signals communicated between the vehicle control system and the remote control system via the communication devices 110.

In one embodiment, the communication devices 110 may provide for much longer ranges of control of the vehicle systems than terrestrial wireless communication devices. For example, the communication devices 110 can allow for a remote control system to communicate with and remotely control vehicle systems over a range of hundreds or thousands of kilometers from the devices 110 and the remote control system. The communication devices 110 may include satellites or devices that communicate with satellites (e.g., antennas and associated transceiving circuitry) that allow for wireless signals to be communicated between the vehicle systems and the remote control system over very large distances of hundreds or thousands of miles or kilometers. This allows for the remote operator to remotely control the movement of a vehicle system without the vehicle system being within eyesight (e.g., the range of vision) of the remote operator (without use of a camera or magnifying device).

The remote operator may control different vehicle systems at different times. For example, during a first period of time, the remote operator may cause the remote control system to generate and communicate signals to the vehicle control system of the vehicle system 102A to control operations (e.g., to change or control a throttle position) of the vehicle system 102A. During a subsequent, second period of time, the remote operator may cause the remote control system to generate and communicate signals to the vehicle control system of the vehicle system 102B to control operations (e.g., to change or control a throttle position) of the vehicle system 102B. The remote operator and remote control system may continue to switch between which vehicle system is controlled during different time periods to allow the remote operator to concurrently control the operations of several different vehicle systems. Optionally, the remote operator and the remote control system can communicate signals to multiple vehicle systems at the same time or during overlapping time periods in order to simultaneously control operations of multiple vehicle systems. The remote control system may control movements of these vehicle systems in an over-the-road environment. For example, instead of the remote control system merely controlling movement of the vehicle systems within a vehicle yard (e.g., a rail yard), the remote control system may control the movements of the vehicle systems along routes that extend between vehicle yards or that are much larger (e.g., longer) than the vehicle yards.

The remote control system may remotely control movements of different vehicle systems based on conditions of the routes on which the vehicle systems are moving. For example, the remote control system may remotely control movement of a vehicle system while that vehicle system is traveling on a first segment of the route that has fewer curves and/or has curves with larger radii of curvature than a different, second segment of the route. Responsive to the vehicle system traveling on the second segment of the route, the remote control system may pass or hand off control of the vehicle system to an onboard operator.

The vehicle control systems onboard the vehicle systems may control the same or other operations of the vehicle systems as the remote control systems. For example, in one embodiment, the remote control system may control the throttle or speed command of a vehicle system during nominal conditions and the onboard operator of the same vehicle system can monitor the vehicle system and change the throttle setting, apply the brakes, or otherwise control operation of the vehicle system in response to identifying an unsafe situation (e.g., the vehicle system moving too fast, an obstruction on the route being traveled by the vehicle system, etc.). Optionally, the remote control system can control or change operation of the vehicle system in response to identifying an unsafe situation (e.g., the vehicle system moving too fast, an obstruction on the route being traveled by the vehicle system, etc.).

Figure 2:
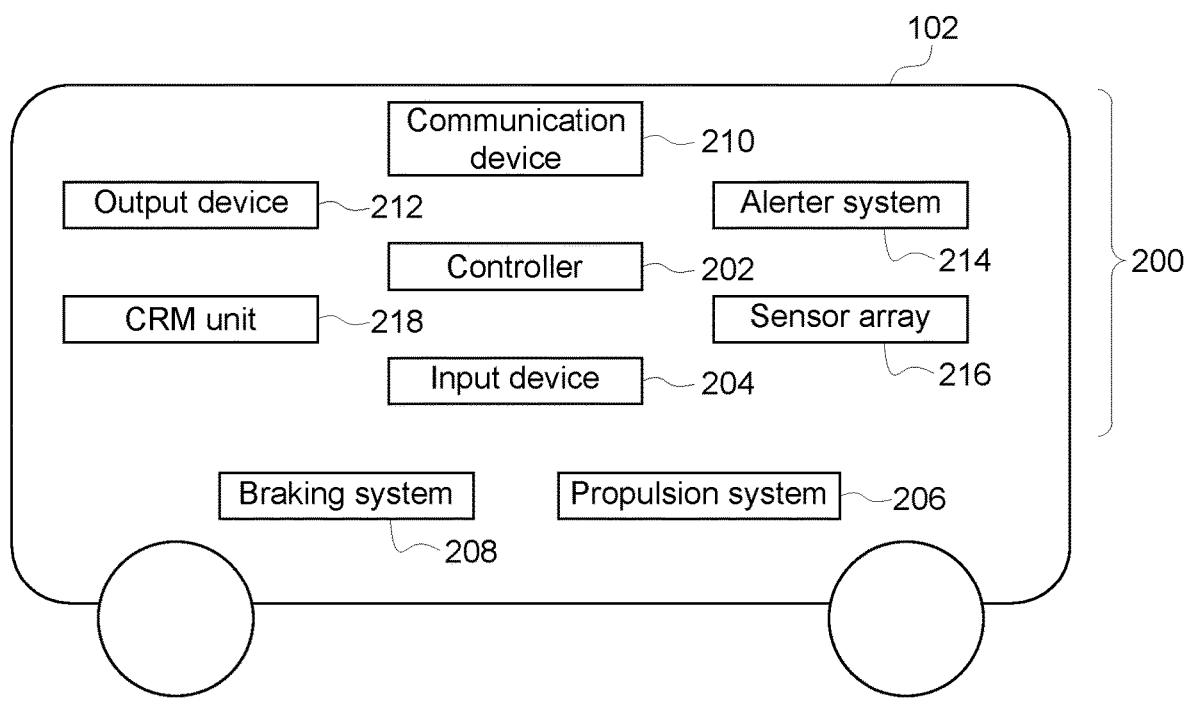
FIG. 2 illustrates one embodiment of a vehicle control system.

FIG. 2 illustrates one embodiment of a vehicle control system 200. The vehicle control system is disposed onboard the vehicle system 102. While the vehicle system 102 is shown as a single vehicle in FIG. 2, optionally, the vehicle system 102 may include multiple vehicles traveling together along a route. The vehicles in a vehicle system may be mechanically coupled with each other or may be mechanically decoupled or separate from each other but communicating with each other to coordinate movements of the vehicles such that the vehicles travel together as a larger vehicle system.

The vehicle control system includes a controller 202, which represents hardware circuitry that includes and/or is connected with one or more processors (e.g., microprocessors, controllers, field programmable gate arrays, and/or integrated circuits) that perform various operations described herein. The controller 202 receives signals from an input device 204 that receives control input from the onboard operator 102 of the vehicle system. The input device 204 can represent one or more throttles (e.g., levers, pedals, etc.), buttons, touchscreens, switches, etc., that control operation of the vehicle system. For example, the input device 204 can be actuated by the onboard operator of the vehicle system to change a throttle setting of a propulsion system 206 to change how quickly the vehicle system is moving, to change a brake setting of a brake system 208, to communicate one or more signals to the remote control system 108 (e.g., via a communication device 210 of the vehicle control system), or to otherwise control operation of the vehicle system.

The propulsion system 206 represents one or more engines, generators, alternators, motors, or the like, that operate to propel the vehicle system. The brake system 208 represents one or more brakes of the vehicle system, such as dynamic brakes, friction brakes, etc. The communication device 210 represents hardware circuitry used for communicating signals with the remote control system, such as one or more antennas, transceivers, routers, or the like. An output device 212 may present information to the onboard operator, such as information representative of operations of the vehicle system (e.g., moving speeds, speed limits, accelerations, temperatures, fuel levels, etc.), information communicated from the remote control system (e.g., speeds at which the vehicle system is to move, locations where the vehicle system is to brake, etc.), or other information. The output device 212 can represent one or more touchscreens (which also may be the input device 204) or other display devices, speakers, haptic devices, etc.

In one mode of operation, the vehicle control system receives control inputs from the remote control system and uses the control inputs to automatically control operation of the vehicle system. The control inputs can designate operations or operational settings or parameters of the vehicle system, such as designated speeds at which the vehicle system is to travel, designated times and/or locations at which the vehicle system is to brake, designated accelerations and/or decelerations at which the vehicle system is to change speeds, locations that the vehicle system is to move toward, designated throttle settings, etc. The controller of the vehicle control system can receive these control inputs from the remote control system via the communication device of the vehicle system and automatically control (e.g., without intervention of the onboard operator) the propulsion system and/or braking system of the vehicle system to implement the control inputs.

The remote control of the vehicle system can provide the onboard or local crew member 102 with more time to focus on other tasks (relative to the onboard or local crew member 102 not having the remote control system available for assisting in controlling movement of the vehicle system). For example, the onboard operator can have additional time to look for obstructions in the path of travel of the vehicle system, to monitor operation of the vehicle system, to perform maintenance, inspection, and/or repair of the vehicle system, or the like. The system 100 can reduce the skill needed to manually control movement of the vehicle system, such as by having the remote control system provide speed inputs and the vehicle control system being used by the operator to control the vehicle system to travel according to the speed inputs.

For example, the remote control system may communicate speed set points, or designated speeds (and/or locations along a route, distances along a route, or times at which the vehicle system is to be traveling as the designated speeds) to the vehicle control system. These speeds may be provided to the vehicle control system as the vehicle control system is moving, in contrast to a previously determined or generated schedule or speed trajectory that is generated prior to movement of the vehicle system. The vehicle control system can receive and report these speeds to the onboard operator, and the onboard operator can actuate the input device onboard the vehicle system to cause the vehicle system to travel according to the designated speeds. Additionally, the onboard operator can safely and efficiently return to controlling movement of the vehicle system should the need arise by providing a speed input to the local control system, such as when the operator at the remote control system is not able to remotely direct movement of the vehicle system, communication delays or interruptions prevent the remote control system from communicating control inputs to the vehicle control system, etc.

The controller of the vehicle control system includes skilled driving knowledge that incorporates vehicle handling and other information used to determine how to change operational settings (e.g., throttle and/or brake settings) of the vehicle system to safely and efficiently control operation of the vehicle system according to the higher-order control inputs provided by the remote control system. For example, the controller may receive operational set points as control inputs from the remote control system and/or from the onboard operator. An operational set point can represent an operational goal that the vehicle system is to achieve, such as a moving speed, a location or distance in which the vehicle system is to stop or slow movement, a location to which the vehicle system is to travel, a time by which the vehicle system is to reach a location, an amount of fuel that the vehicle system is to consume or consume less than during movement, an amount of emissions that the vehicle system is to generate or generate less than during movement, throttle settings or positions, brake settings or positions, etc. The vehicle control system receives the operational set points and changes the settings of the propulsion system and/or braking system of the vehicle system so that the vehicle system achieves the set points.

As one example, the vehicle control system may receive a designated speed at which the vehicle system is to travel from the onboard operator and/or from the remote control system. The controller of the vehicle control system may determine a current speed of the vehicle system (e.g., from a sensor such as a tachometer, global positioning system receiver, etc.) and compare the current and designated speeds to determine how to change the throttle and/or brake settings of the vehicle system to achieve the designated speed. In one example, the controller can determine changes in the throttle and/or brake settings that cause the vehicle system to achieve the designated speed while consuming less fuel and/or generating fewer emissions than using other, different changes in the throttle and/or brake settings (e.g., by switching to the highest throttle setting). In another example, the controller can determine the changes that reduce the number and/or size of throttle and/or brake setting changes relative to other changes, changes in the throttle and/or brake settings that reduce forces exerted on couplers relative to other changes, etc.

The controller can control the propulsion and/or braking systems to try and maintain, on average, the designated set point and/or to use the set point as an upper limit on the operational settings of the vehicle system. The controller can project speeds at which the vehicle system will move (e.g., determine a speed trajectory) based on the current speed and the changes to the throttle and/or brake settings in order to determine how to cause the vehicle system to travel at the set point designated by the remote control system or the onboard operator.

The remote control system may dictate control inputs that control operation of the vehicle system at various levels. For example, the remote operator can use the remote control system to provide varying speed set points during a trip of the vehicle system as a function of locations of the vehicle system such that the set points change at two or more different locations. For example, set points may be communicated to the vehicle control system from the remote control system as: proceed at time 0530, stop at location 123 by time 1400; set out car at siding (with protections and inputs provided by the onboard crew member 102; stop at location 53 until given authorization to move by foreman. A simple language/syntax can be developed for to provide these set points. The controller of the vehicle control system then transforms these set points into a speed command trajectory, which is used to determine the settings of the propulsion and braking systems of the vehicle system.

The vehicle control system may receive the operational set points and determine an operational setting trajectory for a vehicle system based on the operational set points. For example, the controller 202 may receive the speed set points provided by the remote control system and determine the throttle settings and/or brake settings that are to be used by the respective propulsion and braking systems 206, 208 in order for the vehicle system to reach the speed set points. The controller 202 may examine the grades of the route, curvatures of the route, weights of the vehicles and/or cargo, etc., in order to determine the throttle and/or brake settings. For example, for inclined grades and/or heavier vehicles and cargo, larger throttle settings may be needed to accelerate to a faster speed set point than for flatter or declined grades and/or lighter vehicles and cargo. The throttle and/or brake settings may be designated for different locations along the route, distances along the route, and/or times. The controller 202 may then control the propulsion and/or braking systems 206, 208 to implement the throttle and/or brake settings in order to achieve the speed set points.

Optionally, the vehicle control system and/or the onboard operator of the vehicle system can determine the set points of the vehicle system and communicate these set points to the remote control system via the communication device 210. The remote control system may examine the set points and determine the operational settings and/or changes to the operational settings of the vehicle system that can be used to reach or achieve the set points. The operational settings and/or changes in the operational settings may be communicated from the remote control system to the vehicle control system so the controller of the vehicle control system can implement the operational settings and/or changes to the operational settings with the propulsion and/or braking systems.

An alerter system 214 of the vehicle control system monitors physiological features of the onboard operator 102 of the vehicle system to determine whether the onboard operator is alert and able to provide sufficient safeguards against unsafe operation of the vehicle system by the onboard controller and/or the remote control system. The alerter system receives monitoring signals from one or more sensors in a sensor array 216. These sensors can include heart rate monitors, blood pressure monitors, cameras, the input device 204, etc. The alerter system includes or represents hardware circuitry that includes and/or is connected with one or more processors (e.g., microprocessors, field programmable gate arrays, or integrated circuits) that receive and examine the monitoring signals from the sensor array. Based on the monitoring signals, the alerter system can determine whether the onboard operator of the vehicle system is alert and monitoring operations of the vehicle system.

For example, the alerter system can examine the blood pressure and/or pulse or heart rate and rate variation of the operator to determine if the operator is alive and alert. Optionally, the alerter system can examine other sensor data, such as electroencephalogram (EEG) data, electrocardiogram (ECG) data, or other contact/wearable measurements of the operator. The alerter system can receive images or video of the operator to determine whether the operator is moving at least as often as a designated frequency (e.g., once every minute, once every hour, etc.). The alerter system can receive images or video of the operator and use computer or machine vision techniques to determine postures and/or gestures of the operator, such as slouching versus upright, raised eyebrows or closed eyes, yawns or closed mouths, etc., to determine whether the operator is alert.

As another example, the alerter system provides cognitive tasks to the operator (e.g., via the output device 212) and examines the operator's performance of the tasks to determine whether the operator is alert. The cognitive tasks can include directions to play a game (e.g., tic-tac-toe), directions to perform a series of examinations of the vehicle system, directions to actuate a sequence of input devices (e.g., buttons, levers, areas of a touchscreen, etc.), or other tasks that require the operator to be alert to perform the tasks. If the operator does not complete the tasks to at least a specified level of achievement or is unable to complete the tasks, then the alerter system may determine that the operator is not alert. Optionally, the cognitive tasks may be contextual cognitive tasks. These tasks may be similar to the cognitive tasks previously described, but may require the operator to perform tasks related to operation of the vehicle system. For example, the alerter system may direct the operator to manually input (via the input device 204) the current location of the vehicle system, the current ambient temperature, the current weather conditions, the grade of the segment of the route currently being traveled upon, or the like. If the operator is unable to complete the task and/or to perform the task up to at least a designated level (e.g., the operator is unable to finish a game or is unable to beat the game), then the alerter system may determine that the operator is not currently alert.

In one embodiment, the alerter system contextually examines the observed operator behavior (e.g., inputs to local control system) to expected operator behavior generated through an awareness of vehicle context. For example, the alerter system may determine when the vehicle system is approaching a grade crossing and that the expected behavior is for the operator to be attentive to the crossing and place a hand on or near a horn actuator of the vehicle system. If the operator does not behave in this manner, then the alerter system determines that the operator is not alert.

Responsive to determining that the operator is not alert, the alerter system may perform one or more actions. The alerter system may actuate one or more alarms (e.g., lights, speakers, etc.) via the output device 212, the alerter system may direct the controller to automatically reduce the throttle and/or activate the braking system of the vehicle system, the alerter system may communicate a warning signal to the remote control system, the alerter system may switch control of one or more operations of the vehicle system from the onboard operator or vehicle control system to the remote operator or remote control system (e.g., control over the braking system), etc.

Optionally, the alerter system may monitor physiological features of an off-board operator at the remote control system to determine whether the off-board operator is present and alert during remote control of one or more vehicle systems. Responsive to determining that the off-board operator is not present or is not alert, the alerter system may pass or hand off remote control of a vehicle system to another remote operator or to an operator onboard the vehicle system.

In one embodiment, the communication devices 110, 210 and/or the controllers 102, 202 can monitor the communication or data link(s) between the communication devices 110, 210 to determine whether to change how the vehicle system is controlled based on the communication or data link(s). A communication or data link can represent a connection between the communication devices 110, 210 to permit communication of data between the communication devices 110, 210. The link can be disrupted or interrupted due to a variety of causes, such as failure of a communication device 110, 210, travel of the vehicle system through a tunnel or valley, electromagnetic interference from sources external to the vehicle system, etc. The communication or data link between the remote control system and the vehicle system can be monitored by the communication devices 110 and/or 210 and, if the link become interrupted, destroyed, or too limited (e.g., the bandwidth or speed of the link decreases below a designated threshold, such as by decreasing by 50% or more), then the communication devices 110, 210 and/or controllers 102, 202 can assign another remote control system to control and be communicatively coupled with the vehicle system.

The vehicle control system also includes a crew resource management (CRM) unit or console 218. With the vehicle system being controlled using a distributed crew of operators, the CRM unit 218 provides for non-verbal communication between the remote and local operators of the vehicle system. The CRM unit represents hardware circuitry that includes and/or is connected with one or more processors (e.g., microprocessors, integrated circuits, field programmable gate arrays, etc.) that receive signals from the remote operator via the remote control system and the communication device 210, from the onboard operator via the input device 204, from the alerter system 214, from an alerter system of the remote control system, and/or from one or more other locations, and display or otherwise present this information to the onboard operator of the vehicle system. For example, if the onboard or remote operator updates the speed or state of the vehicle system, an indicator light can be activated on the CRM unit 218, which notifies the other operators of the updated speed or state. The CRM unit may require that the operator in the same location of the CRM unit confirm or acknowledge the changed speed or state, such as by actuating the input device 204. This acknowledgement may be communicated to the operators (local and remote) to ensure that all operators are aware of changes in the operations of the vehicle system and are aware that other operators are aware of the changes.

Figure 3:
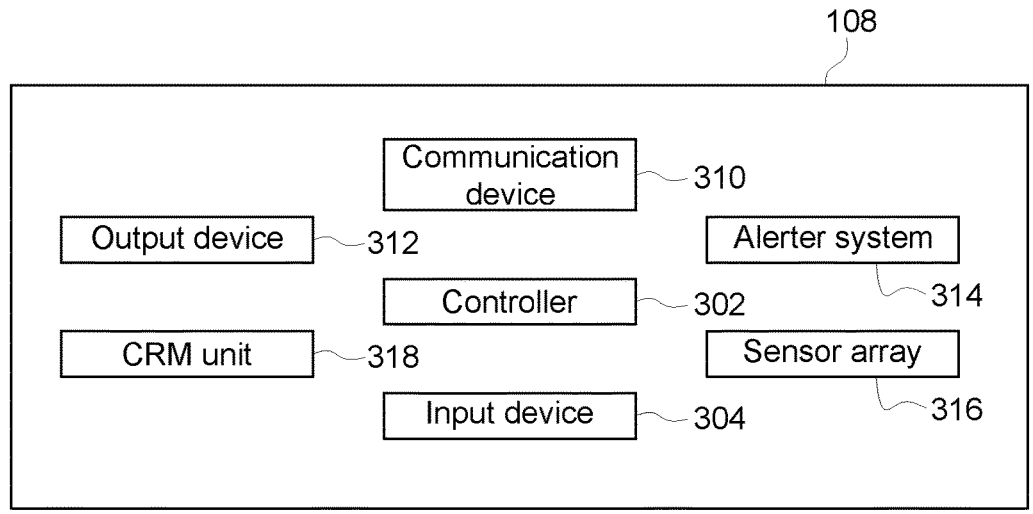
FIG. 3 illustrates one embodiment of a remote control system shown in FIG. 1.

FIG. 3 illustrates one embodiment of the remote control system 108 shown in FIG. 1. The remote control system includes a communication device 310, which may be similar or identical to the communication device 210 of the vehicle control system, to permit the remote and vehicle control systems to communicate with each other. The remote control system also includes a controller 302, which may be similar or identical to the controller 202 of the vehicle control system. The controller 302 may perform the operations of the remote control system described herein. The remote control system also may include an alerter system 314 and sensor array 316 that operate and perform the same or similar functions as described above in connection with the same components of the vehicle control system. This allows the remote control system to determine whether the remote operator at the remote control system is alert. The remote control system also includes an output device 312 similar or identical to the output device 212 of the vehicle control system, and a CRM unit 318 that is identical or similar to the CRM unit 218 of the vehicle control system.

The remote control system can allow a single remote operator to remotely control operations of several vehicle systems and maintain awareness of other relevant vehicle systems. The controller of the remote control system may generate signals for display on the output device to represent current states of various vehicle systems. The remote operator or controller may select a vehicle system to be controlled, and the remote operator may change one or more of the operational settings of the selected vehicle system via an input device 304 of the remote control system, such as by setting a set point for the vehicle system. The controller of the remote control system may then generate a signal representative of the set point for communication to the controller of the vehicle control system to allow for the vehicle system to be controlled. The remote control system and/or remote operator may switch between controlling several different vehicle systems at different times or allow the operator to control multiple vehicle systems at the same time.

The remote operator can have access to significantly more information about the context of the vehicle systems being controlled by the remote control system than any single local operator of a vehicle system in one embodiment. Because the remote control system may be communicating with several vehicle systems at a time, data representing the states of these vehicle systems can be aggregated and presented to the remote operator by the CRM unit 318 via the output device 312. These data include current locations, speeds, and statuses of the vehicle systems and the crew members on the vehicle systems (e.g., from the controller 202, alerter system 214, CRM unit 218, or other data source), the location of each vehicle system relative to each other and other waypoints, and physical aspects of the region of operation (e.g., network switch states, signals from dispatcher, maintenance areas, slippery areas, etc.).

Figure 4:
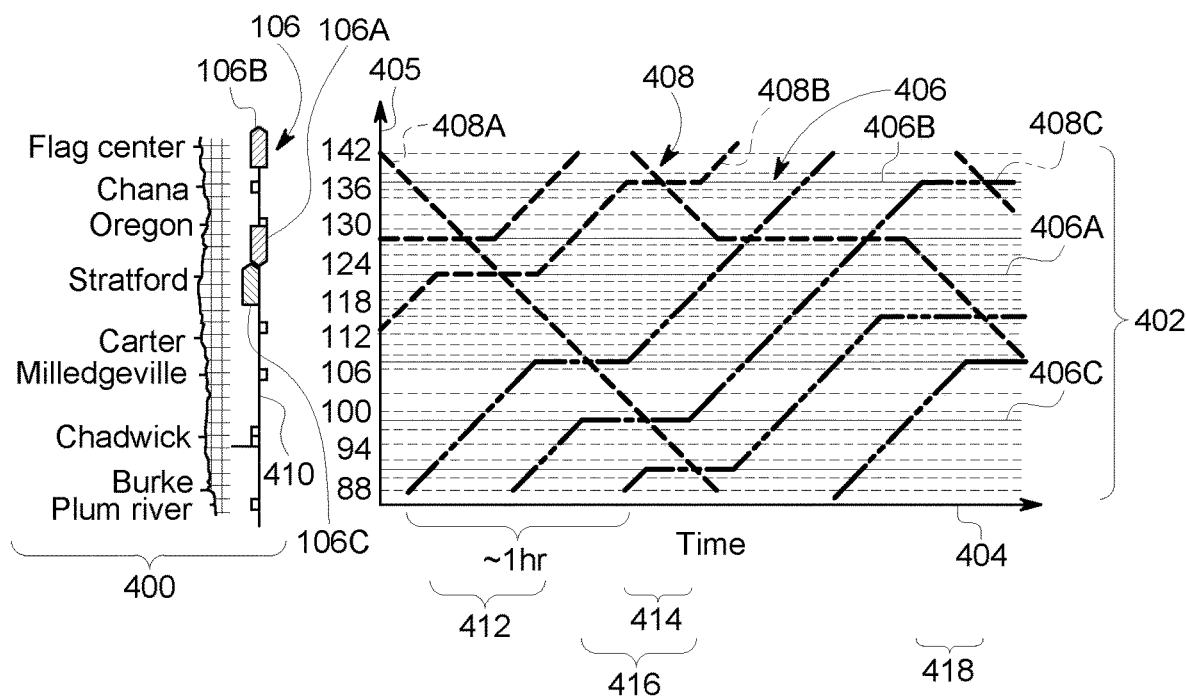
FIG. 4 illustrates one example of a graphical user interface (GUI) presented to an operator of the remote and/or vehicle control system shown in FIG. 1 by a crew resource management unit of the corresponding remote and/or vehicle control system.

FIG. 4 illustrates one example of information presented to an operator of the remote and/or vehicle control system shown in FIG. 1 of the corresponding remote and/or vehicle control system. The information shown in FIG. 4 can be presented on the output device 212, 312, such as a display, to the operator. This information shows an elevation map 400 of the route being traveled by one or more vehicle systems, along with locations of stops and other relevant waypoints along the elevation map 400, locations of vehicle systems 106, and directions of travel of the vehicle systems indicated on or near the elevation map 400 (e.g., by the arrow end of the symbols representing the vehicle systems).

A network status representation 402 can be presented to the operator to indicate the current and future states of the vehicle systems, as estimated or predicted by the controller 302 of the remote control system based on current states of the vehicle systems. The status representation 402 is shown alongside a horizontal axis 404 representative of time and a vertical axis 405 representative of different locations along a selected route being traveled by different vehicle systems. In the illustrated embodiment, several solid lines 406 indicate locations of alternate or siding routes that a vehicle system may move onto to get off of the route shown in the map 400 and allow another vehicle system to pass on the route. Several scheduled movement lines 408 (e.g., movement lines 408A-C) represent estimated, scheduled, or predicted movements of several vehicle systems 106 (e.g., the vehicle systems 106A-C).

For example, a movement line 408A can represent the movement of a first vehicle system 106A along a route 410, a movement line 408B can represent the movement of a second vehicle system 106B along the route 410, and a movement line 408C can represent the movement of a third vehicle system 106C along the route 410. This information presented to the operator by the output device 212 and/or 312 can indicate that the vehicle system 106A is scheduled to travel in a first direction of travel along the route 410 without stopping or pulling off onto any siding routes, while the second vehicle system 106B is to travel in an opposite direction of travel along the same route 410 to a siding represented by the route line 406A, pull off of the route 410 onto the siding 406A and wait for a designated period of time 412, pull back onto the route 410 and travel to another siding represented by the route line 406B, pull off of the route 410 onto the siding 406B and wait for a designated period of time 414, and pull back onto the route 410 and travel along the route 410. This information also indicates that the vehicle system 106C is scheduled to travel in the same direction of travel along the route 410 as the second vehicle system 106B, but at a later time, and to pull off of the route 410 onto a siding 406C and wait for a designated period of time 416, pull back onto the route 410 and travel to the siding 406B, pull off of the route 410 onto the siding 406B and wait for a designated period of time 418, and pull back onto the route 410 and travel along the route 410.

The remote operator may be assigned with controlling movement of the vehicle systems traveling along a designated section of the route 410, such as the portion of the route 410 shown in FIG. 4. Responsive to a vehicle system entering into the section of the route being controlled by a remote operator, the vehicle system may begin being controlled by that remote operator. Prior to the vehicle system entering into this section of the route and after the vehicle system leaves this section of the route, the vehicle system may be controlled by other remote operators. The remote operator in charge of controlling the vehicle systems along the section of the route may concurrently or simultaneously control movements of the vehicle systems while those vehicle systems are on the section of the route.

Figure 5:
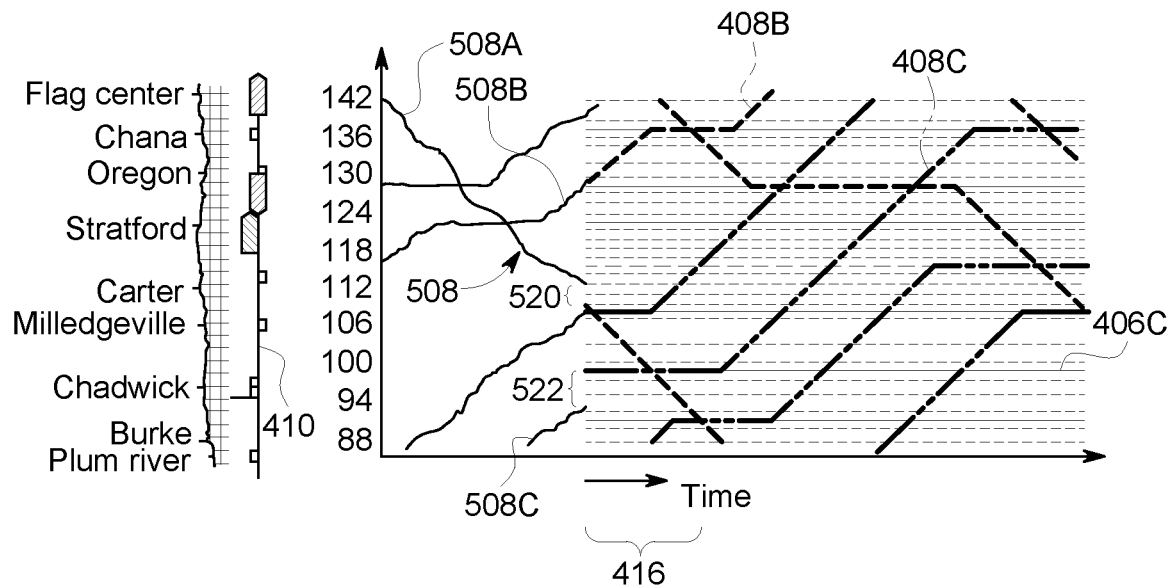
FIG. 5 illustrates another example of a GUI presented to an operator of the remote and/or vehicle control system shown in FIG. 1.

FIG. 5 illustrates another example of information presented to an operator of the remote and/or vehicle control system shown in FIG. 1 by the corresponding output device. The information shown in FIG. 5 is an updated version of the information shown in FIG. 4. For example, as the vehicle systems move along the route 410, the CRM unit can update and display actual locations of the vehicle systems along the route as completed movement lines 508 (e.g., movement lines 508A-C).

Differences 520, 522 between the planned or scheduled movement lines 408 and the actual movement lines 508 can indicate vehicle systems moving ahead of or behind schedule. For example, the difference 520 can indicate that the vehicle system 106A is moving behind schedule along the route 410 and the difference 522 can indicate that the vehicle system 106C is moving along the route 410 even farther behind schedule. This changing information can provide rapidly discernable updates on locations of the vehicle systems to the remote operator who is controlling movements of the vehicle systems. The operator may change how the vehicle systems are controlled based on the information shown by the output device, such as by increasing the speed set points of the vehicle systems 106A, 106C and/or extending the period of time 416 that the vehicle system 106C remains on the siding 406C.

Figure 6:
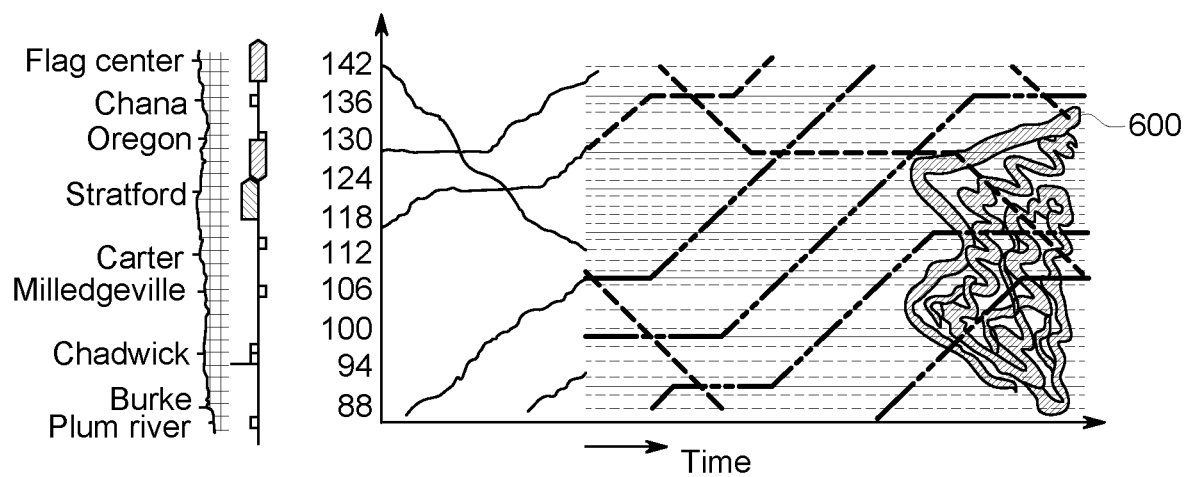
FIG. 6 illustrates another example of a GUI presented to an operator of the remote and/or vehicle control system shown in FIG. 1.

FIG. 6 illustrates another example of information presented to an operator of the remote and/or vehicle control system shown in FIG. 1 by the corresponding output device. The information shown in FIG. 6 is an updated version of the information shown in FIG. 5. For example, as weather conditions change, graphical weather indicators 600 may be overlaid or otherwise shown on the output device 212, 312. In the illustrated embodiment, the weather indicators 600 can represent when and where precipitation (e.g., rain, ice, and/or snow) is predicted by occur, such as by information provided from meteorologists or from other sources. The location of the weather indicators 600 can visually inform the remote operator of when and where weather conditions may impact movement of the vehicle systems. In response to seeing the weather indicators, the operator can change how one or more of the vehicle systems are controlled, such as by slowing movement of the vehicle systems, increasing braking distances of the vehicle systems, etc.

Figure 7:
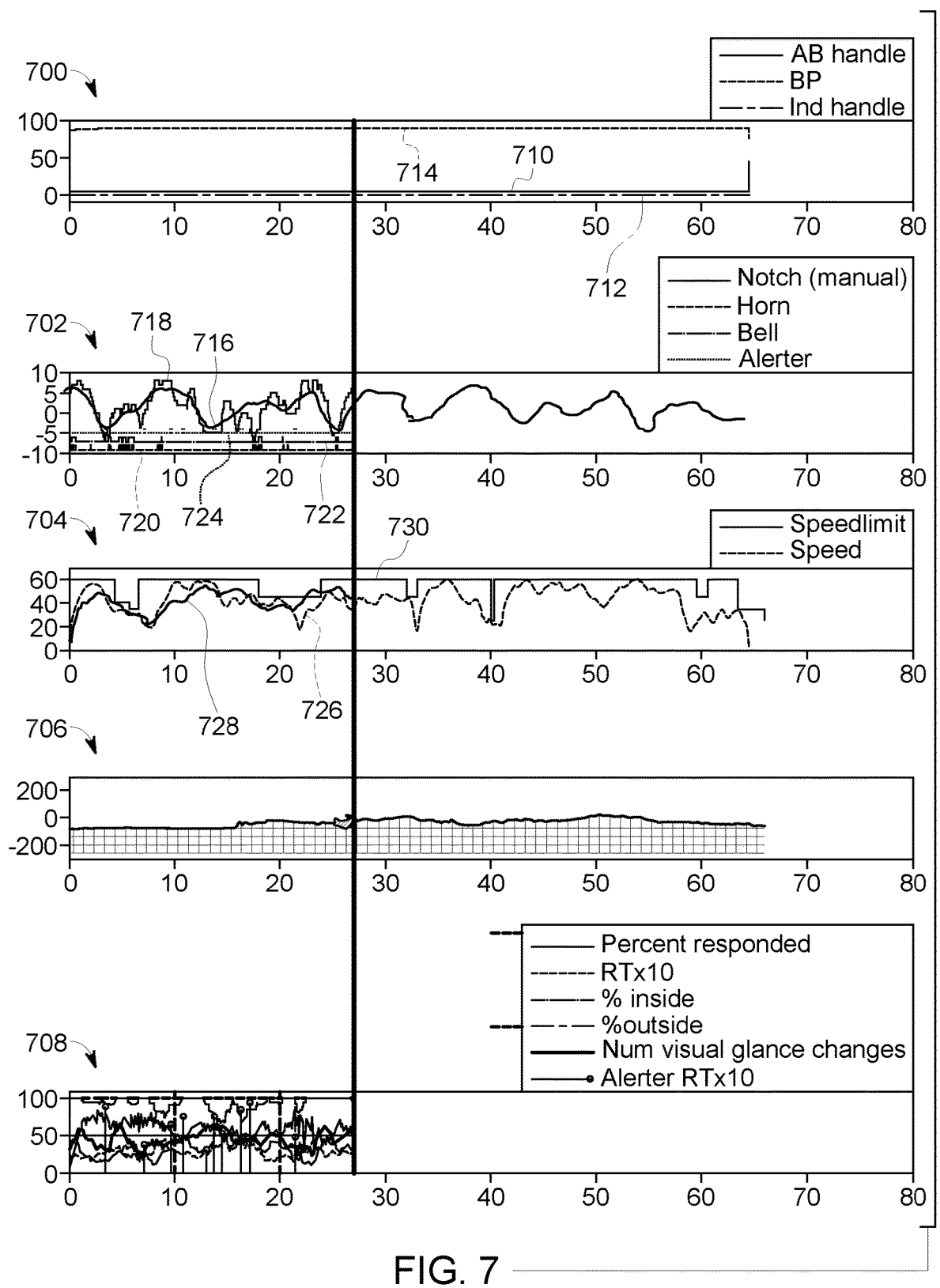
FIG. 7 illustrates another example of information presented to an operator of the remote and/or vehicle control system shown in FIG. 1 by the corresponding output device.
Figure 8:
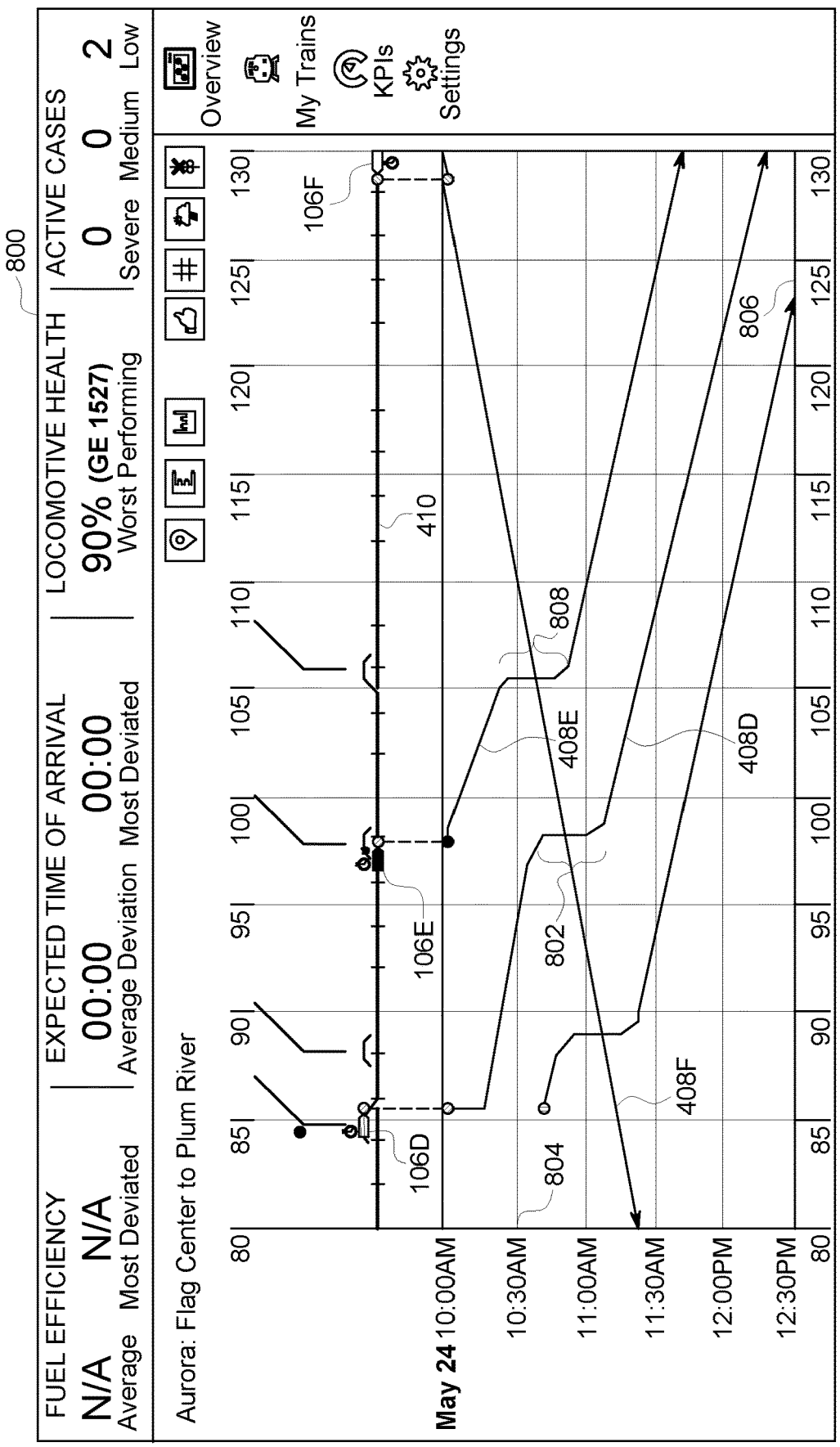
FIG. 8 illustrates an additional example of a GUI presented to an operator of the remote and/or vehicle control system shown in FIG. 1 of the corresponding remote and/or vehicle control system.

FIG. 7 illustrates another example of information presented to an operator of the remote and/or vehicle control system shown in FIG. 1 by the corresponding output device.

The information shown in FIG. 7 represents at least some of the monitoring information obtained by the alerter system of one or more of the remote and/or vehicle control systems and presented to one or more operators via the output device to allow the operators off-board (and, optionally, onboard) the vehicle systems to monitor operations of the vehicle systems and alertness of the onboard operators of the vehicle systems.

An operational setting chart 700 presents settings of the vehicle system at different times. This chart 700 can illustrate, for example, a setting 710 of the braking system of the vehicle system (e.g., the position of an air brake handle), a pressure 712 of air in the braking system of the vehicle system, a position 714 of an individual brake of a vehicle in the vehicle system, and/or other information. The information shown in the chart 700 can be obtained by and/or provided from the controller and/or the CRM unit of the vehicle control system and communicated to the CRM unit of the remote control system via the communication devices 210, 310.

An operational input chart 702 presents the onboard operator-controlled settings of the vehicle system at different times. This chart 702 can illustrate, for example, a designated throttle setting or position 716 (e.g., as determined or dictated by the remote control system and communicated to the vehicle control system), an actual throttle setting or position 718 (e.g., the throttle position actually used by the onboard operator), a horn indicator 720 (e.g., representing if and/or when the horn or other alarm system of the vehicle system is activated), a bell indicator 722 (e.g., representing if and/or when another bell or other alarm system of the vehicle system is activated), and/or an alerter indicator 724 (e.g., represent if and/or when the alerter system onboard the vehicle system detects that the onboard operator is not alert). Alternatively or additionally, other information may be presented. This chart 702 can be examined to determine whether the onboard operator is controlling or attempting to control the vehicle system according to the designated operational settings provided by the remote control system.

A speed chart 704 presents designated moving speeds 726 of the vehicle system (e.g., as determined by the remote control system), speed limits 728 of the route, and actual moving speeds 730 of the vehicle system at different times and/or locations along the route. This chart 704 can be examined by the remote operator to determine if and/or when the vehicle system is violating any speed limits and/or if the vehicle system can move at a faster speed.

An elevation chart 706 presents elevations or grades of the route being traveled by the vehicle systems at different or locations along the route. An operator fatigue chart 708 presents information related to the alertness of the onboard operator. The data used to generate the chart 708 may be obtained by the alerter system and/or vehicle control system. If the chart 708 indicates the alertness of the onboard operator of a vehicle system, then the alerter system onboard the vehicle system can obtain the data used to generate the chart from the sensor array also onboard the vehicle system, and communicate this information to the CRM unit in the remote control system. If the chart 708 indicates the alertness of the off-board operator of the remote control system, then the alerter system of the remote control system can obtain the data used to generate the chart from the sensor array of the remote control system, and communicate this information to the CRM unit onboard one or more vehicle systems and/or in another remote control system. The operators can monitor the information shown in the chart 708 to determine if the remotely located operator (e.g., onboard a vehicle system or at a remote control system) is alert. Examples of the information that can be presented in the chart 708 include percentages of responses obtained from the operator when queried to provide a response by the alerter system, a number of times the glances of the operator changes (e.g., as determined by examining images or video of the operator), or other information.

The data from multiple different charts can be examined and compared to determine if the operator is alert. For example, the charts may have a common (e.g., the same) horizontal axis so that simultaneous events appear at the same locations along the horizontal axes of the charts. As one example, if an operator at a remote control system is monitoring the alertness of an operator onboard a vehicle system, the off-board operator can determine if the fatigue chart 708 indicates that the operator is not alert at the same times as or prior to times when the throttle settings change in the chart 702, and/or if the throttle is being changed later than the designated changes in throttle. If the onboard operator is slow to change the throttle and/or brake settings, is violating speed limits, and/or the alerter system is providing data indicating that the operator is not alert, then the remote control system can generate one or more alarms (e.g., onboard the vehicle system via the output device) to awaken the operator or to cause the operator to become more alert, can automatically slow or stop movement of the vehicle system, can send signals to another vehicle system to approach and/or check on the operator that appears to not be alert, etc.

Distributing at least part of the control system of vehicle systems to an off-board location can allow for a remotely located operator to assist in controlling the movements of several separate vehicle systems. This operator may be able to more easily switch between controlling and/or assisting in the control of multiple vehicle systems than onboard operators, which can allow for the off-board operator to concurrently or simultaneously assist in controlling and/or control multiple vehicle systems. The off-board operator may be replaced by another off-board operator when a contractual or other work shift of the off-board operator ends, which can allow for the vehicle systems to continue moving while not losing the assistance of the off-board operator. Otherwise, the vehicle systems may have to stop for a crew change to allow for the operators having work shifts that are ending to be removed from the vehicle systems and replaced by other operators. Additionally, the off-board operator may be more highly trained, have more specialized training, and/or be more experienced than operators onboard the vehicle system, and this greater experience, higher training, and/or specialized training can allow for the operator to work at the remote control system such that the experience and/or training of the operator is used to control and/or assist in controlling the movement of several different vehicle systems.

In one embodiment, multiple operators at the same and/or different remote control systems can assist in controlling and/or control operations of the same vehicle system. For example, a first off-board operator may control the operational settings of a first propulsion-generating vehicle in the vehicle system while a second off-board operator (at the same or different remote control system) may control the operational settings of a second propulsion-generating vehicle in the same vehicle system. Alternatively, the off-board operators may control different settings of the same vehicle, such as one off-board operator controlling speed, another off-board operator monitoring the alertness of an onboard operator, another off-board operator monitoring brake pressures, etc., of the same vehicle.

The number and/or responsibilities of the off-board operators monitoring and/or controlling a vehicle system can change based on an operational state of the vehicle system, such as when one or more circumstances or scenarios occur. For example, responsive to determining that the vehicle system is entering a more densely populated area (e.g., an urban area) than a previous area, the number of remote operators controlling and/or assisting in controlling the vehicle system may increase. Conversely, responsive to determining that the vehicle system is entering a less densely populated area than a previous area, the number of remote operators controlling and/or assisting in controlling the vehicle system may decrease. As another example, responsive to determining that cargo carried by the vehicle system hazardous and/or has a higher priority than other vehicle systems (e.g., a shipping arrangement for the cargo has a higher value than other shipping arrangements), the number of remote operators controlling and/or assisting in controlling the vehicle system may increase. As another example, responsive to determining that the vehicle system is traveling in an area having increased traffic of other vehicle systems, that one or more components of the vehicle system have failed or are likely to fail, and/or that one or more onboard operators are no longer alert, the number of off-board operators controlling and/or assisting in controlling the vehicle system may increase.

The controller of the remote control system may determine when one or more of these scenarios occur based on data obtained from the vehicle system. For example, the vehicle system may include one or more location determining devices, such as a global positioning system receiver, a radio frequency identification tag reader, a dead reckoning system, or the like, that can report back locations of the vehicle system to the remote control system. The remote control system may have access to the trip manifest of the vehicle system to determine the cargo being carried by the vehicle system. The sensor array can provide data representative of the onboard operator alertness and/or the operational health of components of the vehicle system. Based on this and/or other data, the remote control system can determine when to increase and/or decrease the number of off-board operators to assign to controlling operations of the same vehicle system. In one aspect, the off-board operators may be located at different remote control systems or terminals, and the controller of a remote control system may connect or disconnect the communication device of additional remote control systems with each other and/or the vehicle system to change the number of off-board operators assisting with control of the same vehicle system.

FIGS. 8 through 12 illustrate additional examples of GUIs 800, 900, 1000, 1100, 1200 presented to an operator of the remote and/or vehicle control system shown in FIG. 1 of the corresponding remote and/or vehicle control system. The GUI 800 shown in FIGS. 8 through 12 can be presented on the output device 212, 312, such as a display, to the operator. This GUI shows a horizontal, linear map of a route 410 being traveled by several vehicle systems 106 (e.g., vehicle systems 106D-F), along with locations of stops and other relevant waypoints along the route 410, locations of the vehicle systems 106, and directions of travel of the vehicle systems 106.

A network status representation or map 802 is presented to the operator to indicate the current and future states of the vehicle systems 106, as estimated or predicted by the controller 302 of the remote control system based on current states of the vehicle systems 106. The status representation 802 is shown alongside a horizontal axis 806 representative of different locations along a selected route being traveled by different vehicle systems 106 and alongside a vertical axis 804 representative of time. Several movement lines 408 (e.g., movement lines 408D-F) represent estimated, scheduled, or predicted movements of several vehicle systems 106 (e.g., the vehicle systems 106D-F), similar to as described above. In the illustrated example, the arrow heads on the ends of the movement lines 408 and/or the slope of the movement lines 408 indicate that the vehicle systems 106D, 106E are moving along the route 410 in a left-to-right direction in the perspective of FIGS. 8 through 12 (e.g., a negative slope) and that the vehicle system 106F is moving along the route 410 in an opposite direction (e.g., as indicated by the positive slope). The intersection of the movement lines 408 with different time (e.g., vertical axis 804) and distance (e.g., horizontal axis 806) coordinates indicate where the vehicle systems 106 will be located at different times.

For example, the movement line 408D can represent the movement of a fourth vehicle system 106D along the route 410, the movement line 408E can represent the movement of a fifth vehicle system 106E along the route 410, and the movement line 408F can represent the movement of a sixth vehicle system 106F along the route 410 (in a direction that is opposite that of the direction of movement of the vehicle systems 106D, 106E). The movement line 408D includes a vertical or predominately vertical (e.g., more vertical than horizontal) portion 802. This portion 802 indicates that movement of the vehicle system 106D is paused or at least slowed for a time period over which the portion 802 extends (e.g., along the vertical axis 804). The vehicle system 106D may, for example, pull off of the route 410 onto a siding route or other route for this time period at the location of the portion 802 along the route 410 to allow the vehicle system 106F to pass the vehicle system 106D along the route 410.

The movement line 408E also includes a vertical or predominately vertical portion 808. This portion 808 indicates that movement of the vehicle system 106E is paused or at least slowed for a time period over which the portion 808 extends. The vehicle system 106E may, for example, pull off of the route 410 onto a siding route or other route for this time period at the location of the portion 808 along the route 410 to allow the vehicle system 106F to pass the vehicle system 106E along the route 410.

Passage of the vehicle system 106F by the vehicle systems 106D, 106E as the vehicle systems 106D, 106E are stopped or slowed is shown in the GUI 800 by the movement line 408F of the vehicle system 106F intersecting or crossing over the movement lines 408D, 408E of the vehicle systems 106D, 106E.

The remote operator may be assigned with controlling movement of the vehicle systems traveling along a designated section of the route 410, such as the portion of the route 410 shown in FIGS. 8 through 12. Responsive to a vehicle system entering into the section of the route being controlled by a remote operator, the vehicle system may begin being controlled by that remote operator. Prior to the vehicle system entering into this section of the route and after the vehicle system leaves this section of the route, the vehicle system may be controlled by other remote operators. The remote operator in charge of controlling the vehicle systems along the section of the route may concurrently or simultaneously control movements of the vehicle systems while those vehicle systems are on the section of the route.

Figure 9:
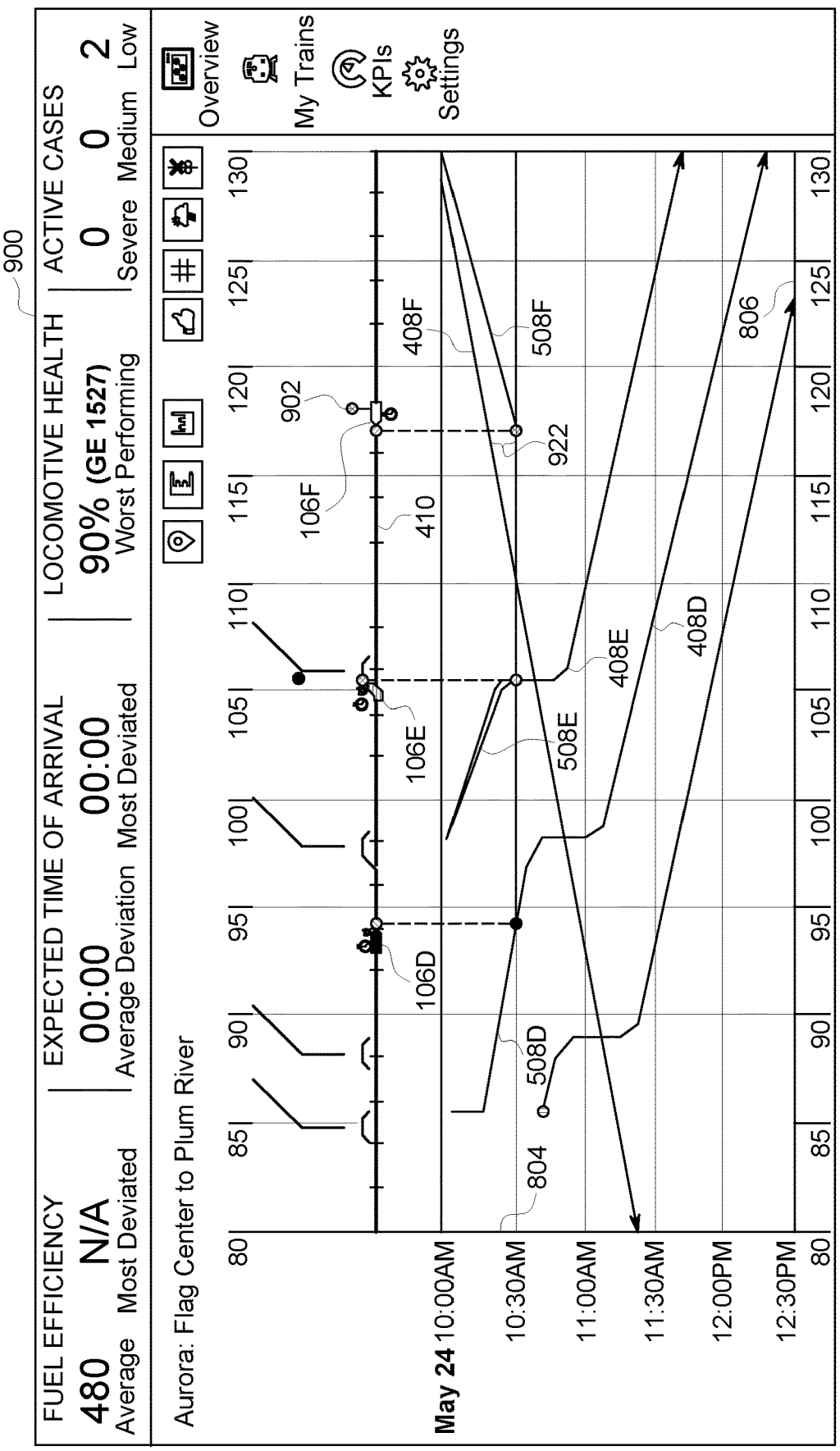
FIG. 9 illustrates an additional example of a GUI presented to an operator of the remote and/or vehicle control system shown in FIG. 1 of the corresponding remote and/or vehicle control system.

FIG. 9 illustrates another example of a GUI 900 shown to an operator of the remote and/or vehicle control system shown in FIG. 1 by the corresponding output device. The GUI 900 represents the current statuses (e.g., relative locations, speeds, etc.) of the vehicle systems 106D-F at a time subsequent to the time represented by the GUI 800 shown in FIG. 8. For example, as the vehicle systems 106 move along the route 410, the CRM unit can update and display actual locations of the vehicle systems 106 along the route as completed movement lines 508 (e.g., movement lines 508D-F). The completed movement lines 508 represent portions of the scheduled movement lines 408D-F that the vehicle systems 106 have completed travel over. The completed movement lines 508 may be shown in a different manner than the scheduled movement lines 408, as shown in FIG. 9.

In the illustrated example, the vehicle system 106F has discovered and/or reported a faulty signal along the route 410 at a fault location 902. This (and/or other faults or factors) may result in the vehicle system 106F traveling behind schedule. The movement of the vehicle system 106F behind schedule is represented by a difference 922 between the scheduled movement line 408F and the completed movement line 508F of the vehicle system 106F, as shown in the GUI 900. The operator of the control system 200 or remote control system 108 may view the GUI 900 to determine the location 902 of the faulty signal (e.g., for re-routing or changing the schedules of one or more other vehicle systems 106 based thereon) and/or that the vehicle system 106F is moving behind schedule.

Figure 10:
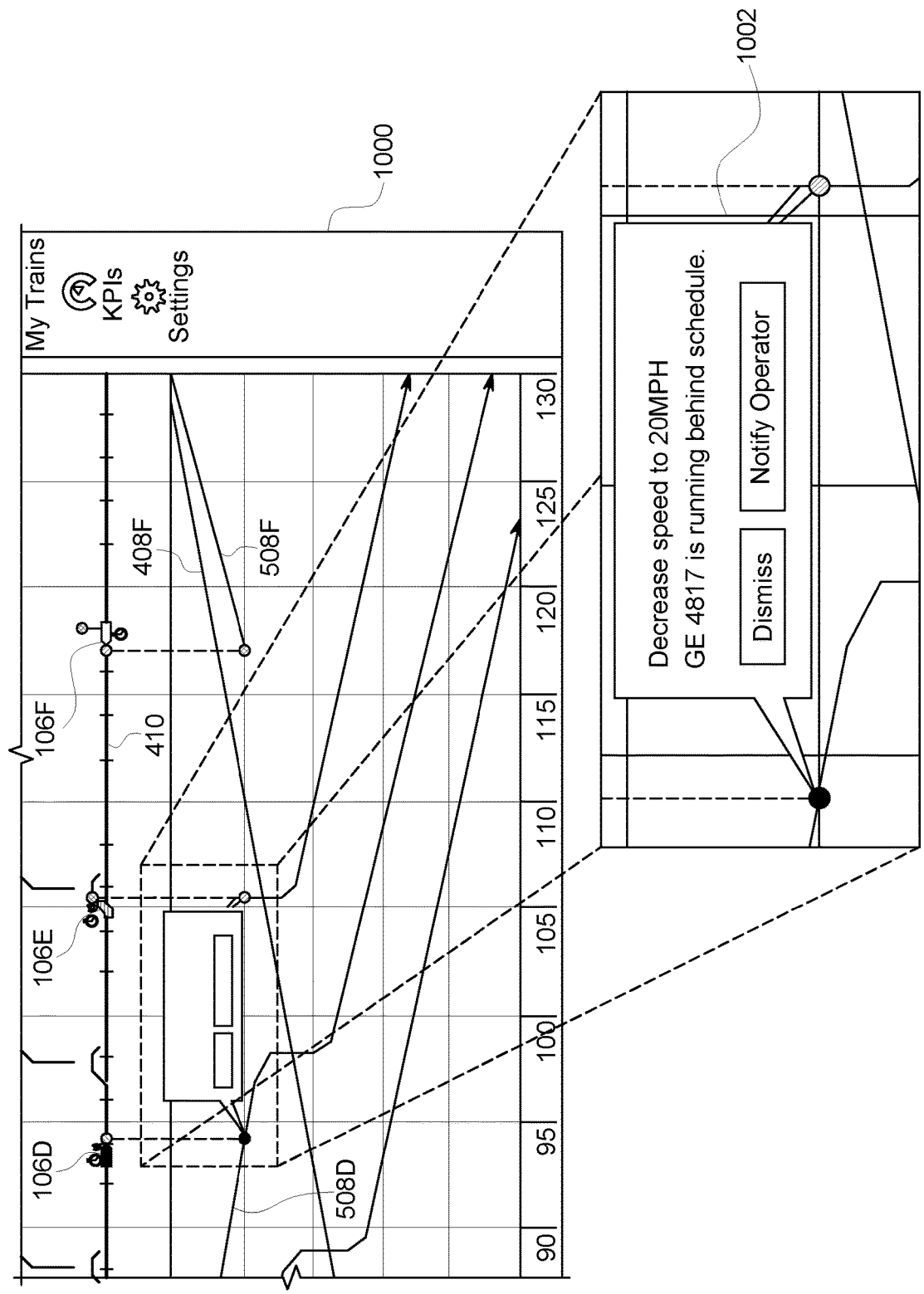
FIG. 10 illustrates an additional example of a GUI presented to an operator of the remote and/or vehicle control system shown in FIG. 1 of the corresponding remote and/or vehicle control system.

FIG. 10 illustrates another example of a GUI 1000 shown to an operator of the remote and/or vehicle control system shown in FIG. 1 by the corresponding output device. The operator of the remote control system 108 may generate a notification 1002 that informs one or more of the vehicle systems 106 of a change or deviation from scheduled movements of the vehicle systems 106. In the illustrated example, the remote control system 108 generates a signal that is wirelessly communicated (and/or communicated via one or more wired connections) to the vehicle system 106D to provide the notification 1002 to the vehicle system 106D. This notification 1002 can direct the vehicle system 106D to change speeds, such as by slowing down (in this example), speeding up, or otherwise deviating from the scheduled movement line 408D for the vehicle system 106D. In response to receiving the notification 1002, the controller 202 of the vehicle system 106D may direct the propulsion system 206 to reduce tractive effort or propulsive force generated by the propulsion system 206 and/or may direct the braking system 208 to increase braking effort generated by the braking system 208.

Figure 11:
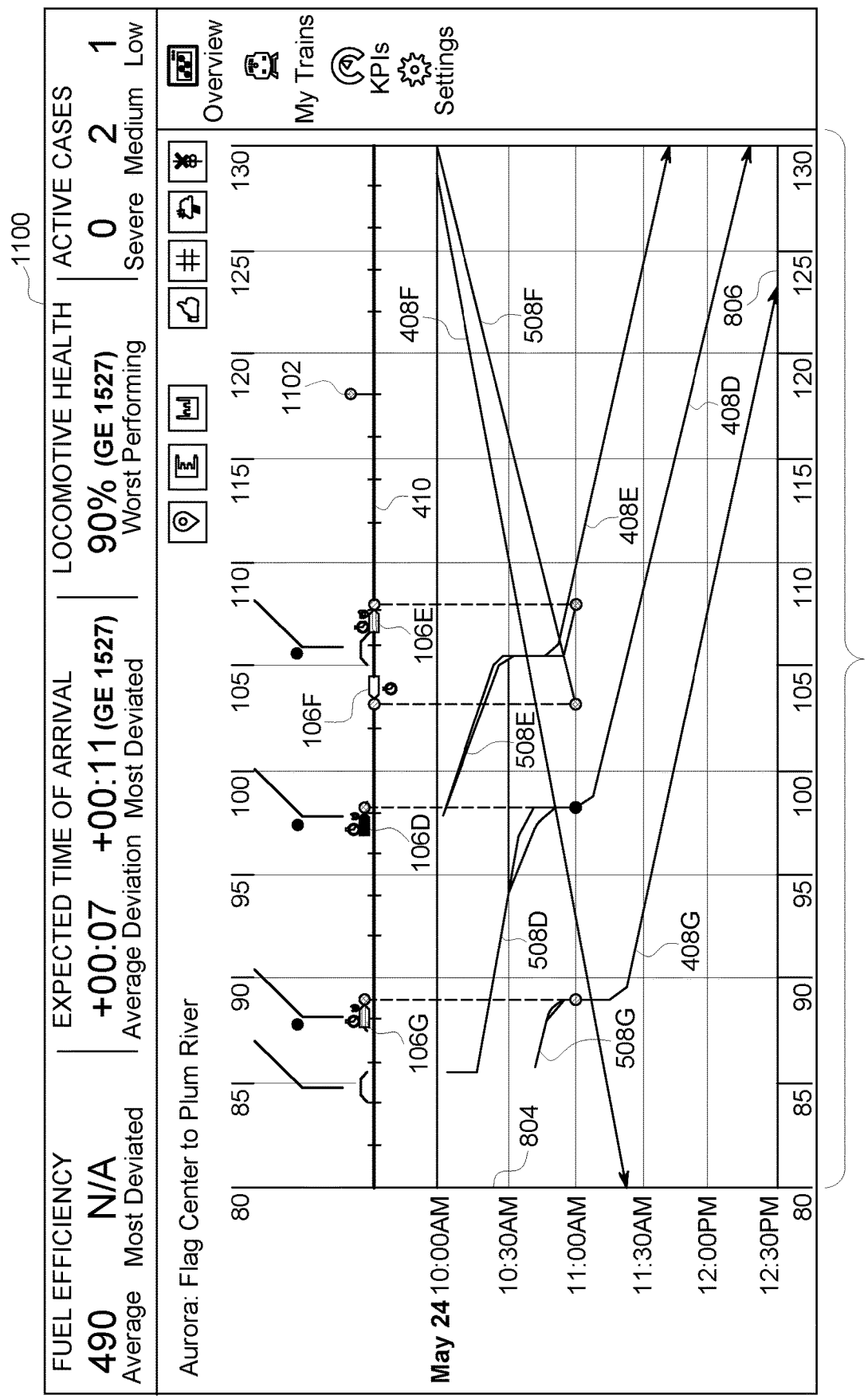
FIG. 11 illustrates an additional example of a GUI presented to an operator of the remote and/or vehicle control system shown in FIG. 1 of the corresponding remote and/or vehicle control system.

FIG. 11 illustrates another example of a GUI 1100 shown to an operator of the remote and/or vehicle control system shown in FIG. 1 by the corresponding output device. The GUI 1100 includes an icon 1102 that represents the location 902 of the faulty signal described above. The GUI 1100 also includes an additional scheduled movement line 408G and a completed movement line 508G for an additional vehicle system 106G. As shown in FIG. 11, the completed movement lines 508D, 508E for the vehicle systems 106D, 106E deviate from the scheduled movement lines 408D, 408E. This can inform the operator that the vehicle systems 106D, 106E are traveling behind schedule. With respect to the vehicle system 106D, the operator may remotely control the vehicle system 106D to speed up to catch up to the scheduled movement line 408D. For example, while the vehicle system 106D slowed down relative to the speeds dictated by the scheduled movement line 408D, the vehicle system 106D may have been sped up by the remotely located operator so that the vehicle system 106D returns to traveling according to the movement line 408D, as shown in FIG. 11.

Figure 12:
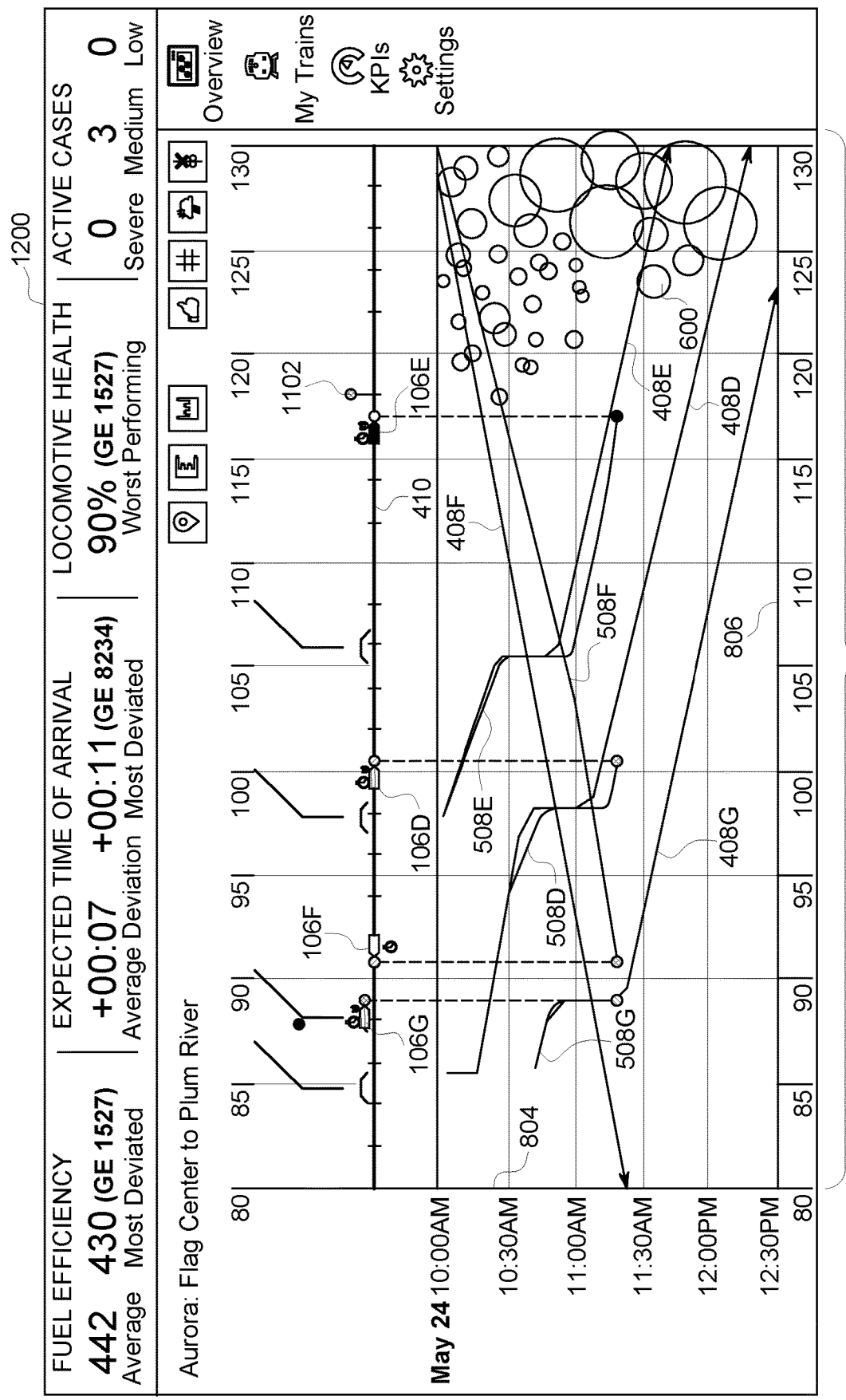
FIG. 12 illustrates an additional example of a GUI presented to an operator of the remote and/or vehicle control system shown in FIG. 1 of the corresponding remote and/or vehicle control system.

FIG. 12 illustrates another example of a GUI 1200 shown to an operator of the remote and/or vehicle control system shown in FIG. 1 by the corresponding output device. The GUI 1200 includes the graphical weather indicators 600 that are overlaid or otherwise shown on the output device 212, 312, as described above. The weather indicators 600 can represent when and where precipitation (e.g., rain, ice, and/or snow) is predicted by occur, such as by information provided from meteorologists or from other sources. The location of the weather indicators 600 can visually inform the remote operator of when and where weather conditions may impact movement of the vehicle systems. In response to seeing the weather indicators, the operator can change how one or more of the vehicle systems are controlled, such as by slowing movement of the vehicle systems, increasing braking distances of the vehicle systems, etc.

Figure 13A:
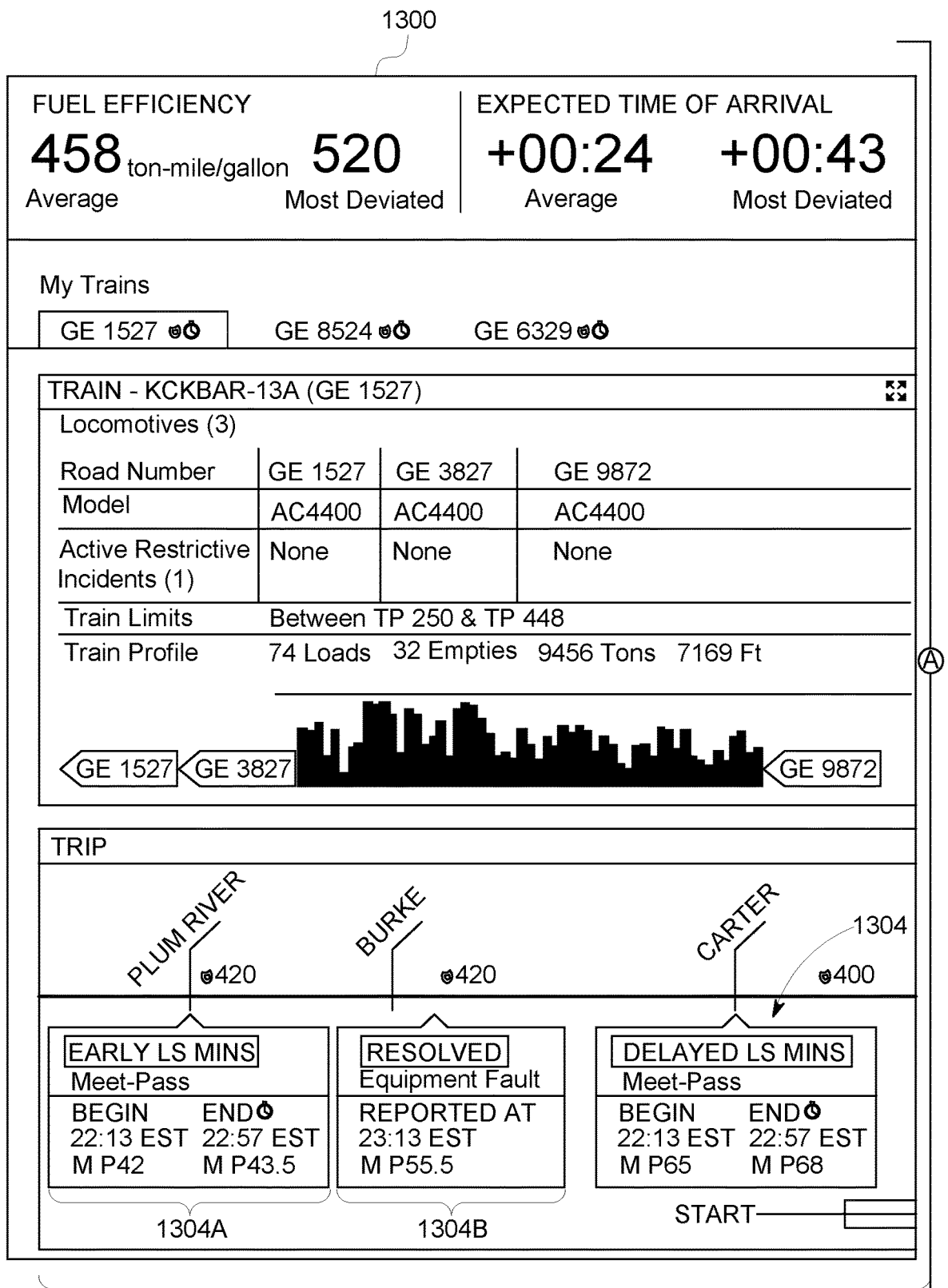
FIGS. 13A and 13B illustrate another example of a GUI shown to an operator of the remote and/or vehicle control system shown in FIG. 1 by the corresponding output device.
Figure 13B:
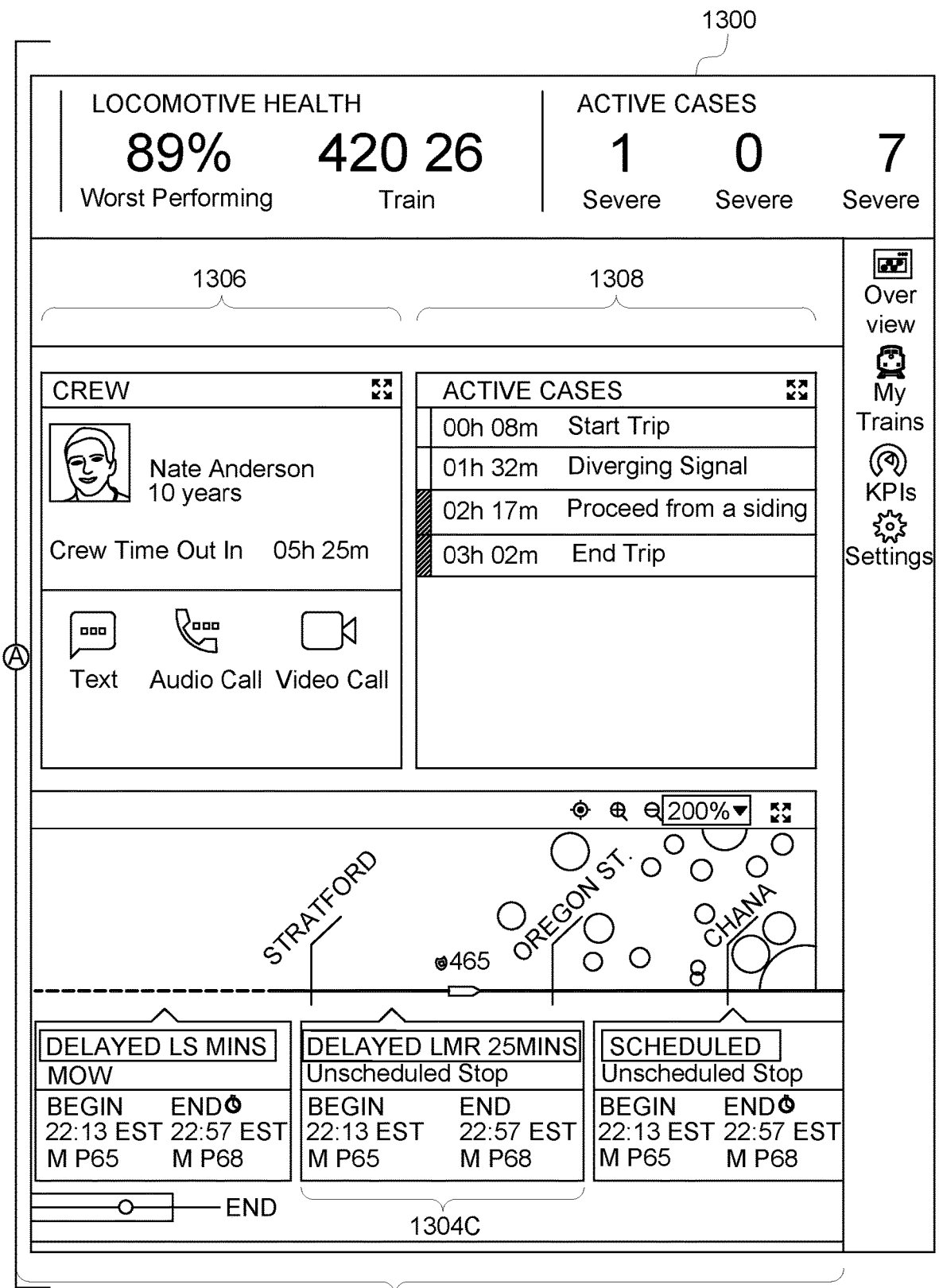

FIGS. 13A and 13B illustrate another example of a GUI 1300 shown to an operator of the remote and/or vehicle control system shown in FIG. 1 by the corresponding output device. The GUI 1300 may be presented to the operator concurrently or simultaneously with presentation of one or more other GUIs described herein (e.g., on different portions of the same output device 312, on different output devices 312, etc.). The GUI 1300 provides a visual representation of a case manager that allows the operator to select different vehicle systems 106 to control based on other information presented on the GUIs described herein. The GUI 1300 presents a map 1302 that indicates a current location of a vehicle system 106. The map 1302 includes icons indicative of scheduled and/or unscheduled events 1304 that the vehicle system 106 has encountered. For example, the icons shown in FIGS. 13A and 13B indicate that the vehicle system 106 arrived early at a meet-and-pass event 1304A, that an equipment failure event 1304B was discovered, that the vehicle system 106 performed an unscheduled stop event 1304C, and so on.

The GUI 1300 can serve as a case manager to allow a remote operator (represented by an operator display portion 1306) to select different vehicle systems to be remotely controlled by the remote operator. Icons indicative of scheduled events 1308 of the vehicle system 106 that is selected by the operator are displayed to the remote operator. In the illustrated example, the operator can view these icons to determine which actions that the operator is to achieve by remotely controlling movement of the vehicle system 106 (e.g., start a trip at a scheduled time, reach a signal at a diverging route, proceed from a siding section of route, and end the trip at a scheduled time). The operator can use these icons as a sort of checklist to ensure that the scheduled actions of the vehicle system 106 are completed.

Figure 14:
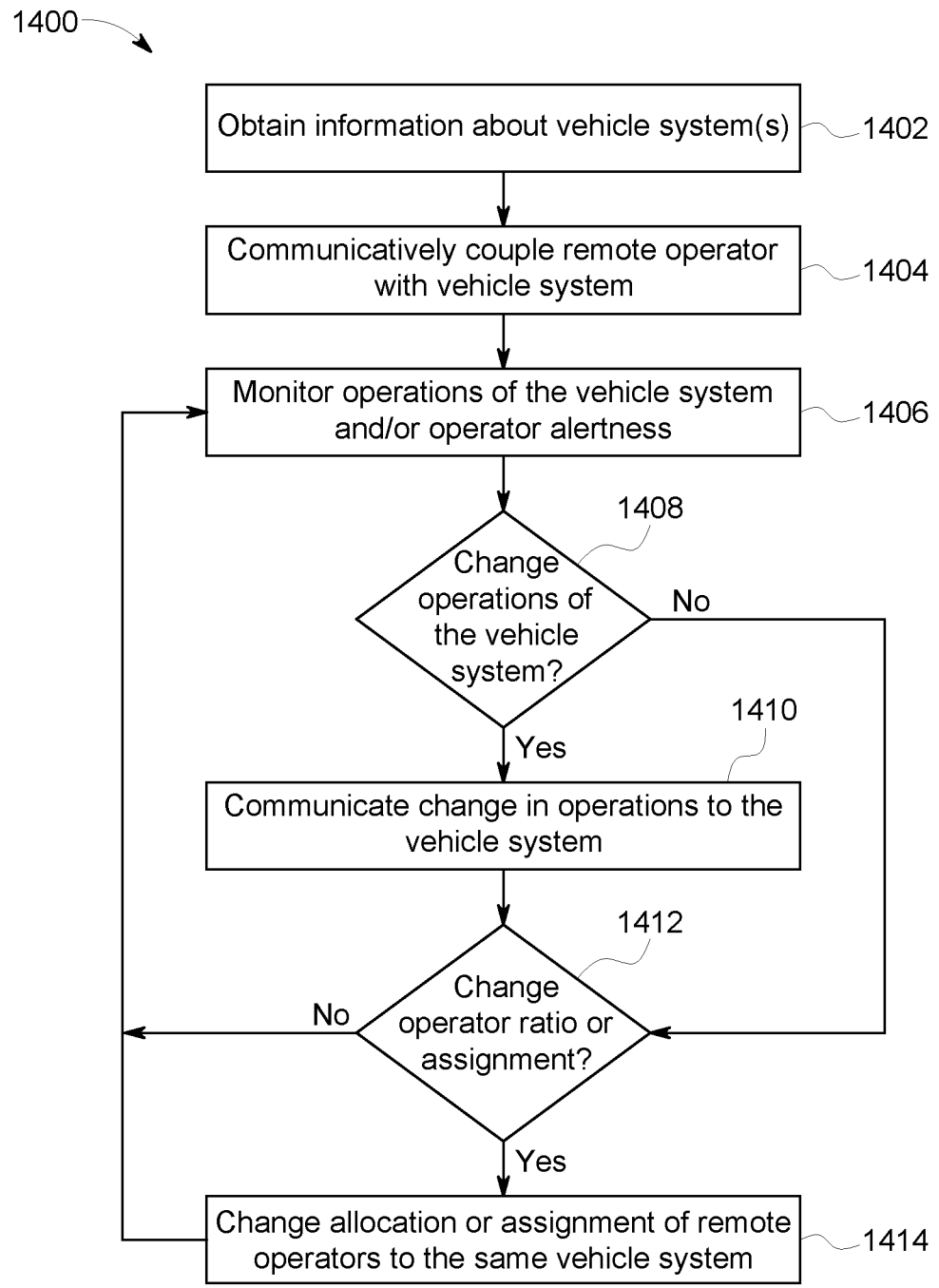
FIG. 14 illustrates a flowchart of one embodiment of a method for distributed vehicle system control.

FIG. 14 illustrates a flowchart of one embodiment of a method 1400 for distributed vehicle system control. The method 1400 may be performed by one or more embodiments of the system 100 shown in FIG. 1. For example, the method 1400 can represent operations performed by one or more of the components of the vehicle control system and/or the remote control system (such as the controllers, the alerter systems, the CRM units, etc.), as described above. In one embodiment, the method 1400 may represent or be used to create a software program for directing the operations of the vehicle control system and/or the remote control system.

At 1402, information about one or more vehicle systems that are to be remotely controlled is obtained. This information can include make up information, which indicates or represents the vehicles in the vehicle systems (e.g., by model number, road number, horsepower capability, braking capability, etc.), the cargo carried by the vehicle systems, the scheduled routes to be taken by the vehicle systems, the schedules of the vehicle systems, etc. This information may be received from a variety of sources, such as a dispatch or scheduling facility, the vehicle systems themselves, or the like.

At 1404, a remote operator is communicatively coupled with at least one vehicle system. For example, the remote control system can communicate one or more signals with the vehicle control system of the vehicle system via a communication network that includes and/or is formed from the communication devices 110 (shown in FIG. 1). The assignment of which remote operator is to be communicatively coupled with the vehicle systems may be made based at least in part on the information received at 1402. Different off-board or remote operators may be associated with different geographic areas. For example, the vehicle systems traveling through a geographic area associated with a remote operator may be assigned to, communicatively coupled with, and remotely controlled by that remote operator during travel through that geographic area. But, the vehicle systems may be assigned to another, different remote operator responsive to exiting that geographic area or entering into another geographic area associated with the other, different remote operator. This can allow for different operators to become familiar with or have increased expertise with controlling movement of a vehicle system through different areas (relative to other operators), and assigning those operators to control the vehicle systems traveling in the areas associated with the operators.

At 1406, operations of the vehicle system and/or operator alertness are monitored. The operations of the vehicle system that are monitored can include throttle positions, brake settings, speeds, accelerations, etc. The operator alertness can be monitored by measuring physiological conditions of an onboard operator, such as respiration rate, heart rate, movements, glances, etc. In one aspect, 1406 can include receiving information from one or more operational systems and/or off-board systems. For example, the operations of the vehicle system may be monitored by receiving information about the vehicles and/or cargo included in the vehicle system.

At 1408, a determination is made as to whether operations of the vehicle system are to be changed. This determination may be made based on the vehicle system operations and/or the operator alertness that are monitored. For example, if the vehicle system is moving faster or slower than a designated speed, is operating with a different throttle and/or brake setting than designated by the remote control system, or is otherwise deviating from a designated operation, the remote control system may determine to change the operation of the vehicle system to return the vehicle system to moving according to the designated operation. As another example, if the onboard operator is no longer alert, then the remote control system may decide to activate an alarm to contact the onboard operator, to change movement of the vehicle system, or otherwise modify how the vehicle system is operating. If operation of the vehicle system is to be changed, then flow of the method 1400 can proceed toward 1410. Otherwise, flow of the method 1400 can proceed toward 1412.

At 1410, the change in operation in the vehicle system is communicated from the remote control system to the vehicle control system. This change in operation may be communicated as a designated set point or other instruction that is communicated via the communication devices 110 to the vehicle control system. At 1412, a determination is made as to whether the operator ratio or assignment of the vehicle system is to be changed. The operator ratio represents the number of off-board operators controlling operations of the vehicle system. For example, an operator ratio may be calculated as the number of off-board or remote operators to the number of onboard operators controlling movement of the vehicle system, the number of off-board or remote operators to the total number of off-board and onboard operators controlling movement of the vehicle system, or another number. The operator ratio can be changed responsive to a change in operational circumstances or scenarios. For example, responsive to determining that the vehicle system is entering a more densely populated area than a previous area, the number of remote operators controlling and/or assisting in controlling the vehicle system may increase. Responsive to determining that cargo carried by the vehicle system hazardous and/or has a higher priority than other vehicle systems, the number of remote operators controlling and/or assisting in controlling the vehicle system may increase. As another example, responsive to determining that the vehicle system is traveling in an area having increased traffic of other vehicle systems, that one or more components of the vehicle system have failed or are likely to fail, and/or that one or more onboard operators are no longer alert, the number of off-board operators controlling and/or assisting in controlling the vehicle system may increase. This may be done automatically by the remote and/or vehicle control system or manually by a supervisor or consensus of the remote operators.

In addition or as an alternate to changing the operator ratio, the operator assignment may be modified. The operator assignment is the indication of which vehicle system is being at least partially monitored and/or controlled by a remote operator. A remote operator can be assigned to several vehicle systems, as described above. The assignment of a remote operator to a vehicle system can be determined by the remote control system, such as by determining which vehicle systems are traveling in (and/or are scheduled to travel into or through) a geographic area (e.g., geo-fence) associated with a remote operator (and then assigning those vehicle systems to the remote operator). As another example, the assignment of a remote operator can be determined based on which skills are needed to remotely control a vehicle system. Some vehicle systems may be carrying hazardous cargo, may be traveling through difficult terrain (e.g., a series of curves, urban areas, etc.), may be more difficult to control relative to other vehicle systems (e.g., due to the number of propulsion-generating vehicles, the weight of the cargo and/or vehicles, the age of the vehicles, etc.), may have systems or controls that require specialized training, or otherwise may require a set of skills that not all operators have. As another example, the assignment of a remote operator can be determined based on a work history of the operator. An operator that has remotely monitored and/or controlled a particular vehicle system or a particular type of vehicle (e.g., based on model number, age, etc., of the propulsion-generating vehicles in the vehicle system) more than another operator may be assigned to remotely control that same vehicle system or type of vehicle system instead of the other operator. As another example, the assignment of a remote operator can be determined based on a current working shift of the operator. For example, if a remote operator is nearing the end of a contractually agreed upon or assigned work shift, another remote operator that has more available time during his or her work shift may be assigned to a vehicle system to avoid exceeding the work shift.

If the operator ratio or assignment is to change, then flow of the method 1400 may proceed toward 1414. Otherwise, flow of the method 1400 can return toward 1406. The method 1400 may proceed in a loop-wise manner until terminated, until completion of a trip of the vehicle system, and/or until a vehicle system being remotely controlled leaves the section of the route being controlled by the remote control system.

At 1414, an allocation or assignment of remote operators controlling the same vehicle system is changed. For example, if the determination at 1412 reveals that more remote operators are needed to remotely control movement of a vehicle system, then one or more additional remote operators begin remotely controlling movement of the vehicle system. Conversely, if the determination at 1412 reveals that fewer remote operators are needed to remotely control movement of a vehicle system, then one or more remote operators currently controlling movement of the vehicle system are assigned to other tasks that do not include remotely controlling movement of the vehicle system.

In one embodiment, a distributed control system includes a remote control system configured to be communicatively coupled with plural separate vehicle systems. The remote control system is configured to remotely control operation of the vehicle systems and/or communicate with the local vehicle control system or operator. The remote control system also is configured to one or more of change how many of the vehicle systems are concurrently controlled by the remote control system or change how many remote operators of the remote control system concurrently control the same vehicle system of the vehicle systems.

In one example, the remote control system is configured to control the operation of the vehicle systems without any operator disposed onboard the vehicle systems during movement of the vehicle systems.

In one example, the remote control system is configured to control the operation of the vehicle systems by designating operations of the vehicle systems and communicating instructions to onboard operators of the vehicle systems to implement the designated operations. The designated operations include one or more of designated throttle positions, designated brake settings, or designated speeds.

Optionally, the remote control system is configured to remotely control the movements of the vehicle systems by providing operating parameters and limits on the movements of the vehicle systems. The operating parameters can include one or more of designated speeds, designated throttle settings, or designated brake settings. The limits can include one or more of designated upper limits on speeds, designated upper limits on throttle settings, designated lower limits on speeds, or designated lower limits on throttle settings.

In one example, the remote control system is configured to change a number of vehicle systems the remote operator concurrently controls based on an operating state of the vehicle systems being concurrently controlled or based on operator input.

In one example, the operating state includes the vehicle system entering into or approaching a particular geographic region of interest.

In one example, the operating state includes the vehicle system transporting hazardous cargo or has another high-risk attribute.

In one example, the remote control system is configured to remotely control the operation of the vehicle systems via one or more wireless networks.

In one example, the remote control system is configured to remotely control the operation of the vehicle systems by designating operational set points that vehicle control systems disposed onboard the vehicle systems are to one or more of maintain or use as upper limits on operations of the vehicle systems.

In one example, the remote control system includes an alerter system configured to obtain sensor data from one or more sensor arrays that monitor one or more of physiological conditions of one or more onboard operators or off-board operators of the vehicle systems or movements of the one or more onboard operators or off-board operators. The alerter system is configured to determine whether the one or more onboard operators or off-board operators are controlling the operation of the vehicle system based on the sensor data.

In one example, the sensor data includes one or more of images or video of the one or more onboard operators or off-board operators.

In one example, the sensor data includes one or more of pulse rates, respiration rates, blood pressures, or movements of the one or more onboard operators or off-board operators.

In one example, the sensor data includes one or more of electroencephalogram (EEG) data, electrocardiogram (ECG) data, or other contact/wearable measurements of the one or more onboard operators or off-board operators.

In one example, the alerter system is configured to obtain the sensor data from the one or more sensor arrays that monitor the one or more physiological conditions of one or more onboard operators. The alerter system can be configured to communicate the sensor data to one or more off-board operators at the remote control system.

In one example, the alerter system is configured to obtain the sensor data from the one or more sensor arrays that monitor the one or more physiological conditions of one or more off-board operators. The alerter system can be configured to communicate the sensor data to one or more onboard operators at the remote control system.

In one example, the alerter system is configured to examine the sensor data and expected operator behavior representative of operator awareness in a vehicle context.

In one example, the remote control system is configured to receive make up information of at least one of the vehicle systems from a dispatch facility and to be assigned to remotely control the at least one of the vehicle systems based on the make up information. In one embodiment, a method includes communicatively coupling a remote control system with plural separate vehicle systems, generating control inputs from the remote control system to remotely control operation of the vehicle systems, and one or more of changing how many of the vehicle systems are concurrently controlled by the remote control system or changing how many remote operators of the remote control system concurrently control the same vehicle system of the vehicle systems.

In one example, the method also includes remotely controlling the operation of the vehicle systems by communicating the control inputs to the vehicle systems without any operator disposed onboard the vehicle systems during movement of the vehicle systems.

In one example, the control inputs designate operations of the vehicle systems. The method also can include communicating the control inputs to onboard operators of the vehicle systems to implement the designated operations. The designated operations can include one or more of designated throttle positions, designated brake settings, or designated speeds.

In one example, the method also includes changing a number of the remote operators that concurrently control the same vehicle system of the vehicle systems based on an operating state of the vehicle system being concurrently controlled.

In one example, the operating state includes the vehicle system entering into or approaching a densely populated area.

In one example, the operating state includes the vehicle system transporting hazardous cargo.

In one example, the method also includes communicating the control inputs from the remote control system to the vehicle systems via one or more satellites.

In one example, the control inputs include designated operational set points that vehicle control systems disposed onboard the vehicle systems are to one or more of maintain or use as upper limits on operations of the vehicle systems.

In one example, the method also includes monitoring one or more of physiological conditions of onboard operators of the vehicle systems or movements of the onboard operators, and determining whether one or more of the onboard operators are controlling the operation of the vehicle system based on the sensor data.

In one example, the sensor data includes one or more of images or video of the onboard operators.

In one example, the sensor data includes one or more of pulse rates, respiration rates, blood pressures, or movements of the onboard operators.

In one embodiment, a distributed control system includes a vehicle control system configured to be disposed onboard a vehicle system formed from one or more vehicles. The vehicle control system is configured to control movement of the vehicle system. The distributed control system also includes a remote control system configured to be communicatively coupled with the vehicle control system. The remote control system is configured to communicate control inputs from one or more off-board operators of the remote control system to the vehicle system in order to remotely control the movement of the vehicle system. The remote control system is configured to change how many of the off-board operators concurrently generate the control inputs for communication from the remote control system to the vehicle control system for remote control of the vehicle system.

In one embodiment, a vehicle control system includes a controller configured to be disposed onboard a vehicle system and to be communicatively coupled with one or more of a propulsion system or a braking system of the vehicle system. The controller is configured to receive operational set points designated by an operator located onboard the vehicle system and to determine operational settings of the one or more of the propulsion system or the braking system that drives the vehicle system to move according to the operational set points designated by the operator.

In one example, the operational set points include designated speeds.

In one example, the operational settings include throttle positions.

As used herein, an element or step recited in the singular and proceeded with the word "a" or "an" should be understood as not excluding plural of said elements or steps, unless such exclusion is explicitly stated. Furthermore, references to "one embodiment" of the presently described subject matter are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the subject matter set forth herein without departing from its scope. While the dimensions and types of materials described herein are intended to define the parameters of the disclosed subject matter, they are by no means limiting and are exemplary embodiments. Many other embodiments will be apparent to those of skill in the art upon reviewing the above description. The scope of the subject matter described herein should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose several embodiments of the subject matter set forth herein, including the best mode, and also to enable a person of ordinary skill in the art to practice the embodiments of disclosed subject matter, including making and using the devices or systems and performing the methods. The patentable scope of the subject matter described herein is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

What is claimed is:

1. A distributed control system comprising:
a remote control system configured to be communicatively coupled with plural separate vehicle systems, the remote control system configured to remotely control different operations of each of the vehicle systems,
the remote control system configured to determine that a remote operator ratio needs to change based at least in part on one or more characteristics of a common vehicle system of the vehicle systems, the remote operator ratio representative of a number of remote operators of the remote control system configured to concurrently control one or more different operations of the common vehicle system,
the remote control system configured to change the remote operator ratio responsive to determining that the remote operator ratio needs to change, wherein changing the remote operator ratio changes one or more of how many of the remote operators concurrently control the one or more of the different operations of the common vehicle system or which of the remote operators are assigned to concurrently control the one or more of the different operations of the common vehicle system.

2. The distributed control system of claim 1, wherein the remote control system is configured to control the different operations of the vehicle systems without any operator disposed onboard the vehicle systems during movement of the vehicle systems.

3. The distributed control system of claim 1, wherein the one or more characteristics of the common vehicle system includes an operating state of the common vehicle system, wherein the operating state of the common vehicle system includes one or more of:
the common vehicle system entering into or approaching a particular geographic region of interest, or
the common vehicle system transporting hazardous cargo.

4. The distributed control system of claim 1, wherein the remote control system is configured to remotely control movements of the vehicle systems by providing operating parameters and limits on the movements of the vehicle systems.

5. The distributed control system of claim 4, wherein the operating parameters include one or more of designated speeds, designated throttle settings, or designated brake settings.

6. The distributed control system of claim 4, wherein the limits include one or more of designated upper limits on speeds, designated upper limits on throttle settings, designated lower limits on speeds, or designated lower limits on throttle settings.

7. The distributed control system of claim 1, further comprising an alerter system configured to obtain sensor data from one or more sensor arrays that monitor a physiological condition of an onboard operator of at least one of the vehicle systems, the alerter system configured to determine whether the onboard operator is controlling one or more of the different operations of the at least one of the vehicle systems based on the sensor data.

8. The distributed control system of claim 7, wherein the sensor data includes one or more of:
images or video of the onboard operator,
a pulse rate, a respiration rate, a blood pressure, or a movement of the onboard operator, or
electroencephalogram (EEG) data or electrocardiogram (ECG) data of the onboard operator.

9. The distributed control system of claim 7, wherein the alerter system is configured to communicate the sensor data to the remote control system.

10. The distributed control system of claim 1, wherein the vehicle systems are mechanically separated from each other.

11. The distributed control system of claim 1, wherein the remote control system is configured to stop movement of at least one of the vehicle systems responsive to the remote control system communicatively decoupling from the at least one of the vehicle systems.

12. A method comprising:
communicatively coupling a remote control system with plural separate vehicle systems, the plural separate vehicle systems mechanically separated from each other;
generating control inputs from the remote control system to remotely control different operations of the vehicle systems;
determining that a remote operator ratio needs to change based at least in part on one or more characteristics of a common vehicle system of the vehicle systems, the remote operator ratio representative of a number of remote operators of the remote control system configured to concurrently control one or more different operations of the common vehicle system; and
changing the remote operator ratio responsive to determining that the remote operator ratio needs to change, wherein changing the remote operator ratio changes one or more of how many of the remote operators concurrently control the one or more of the different operations of the common vehicle system or which of the remote operators are assigned to concurrently control the one or more of the different operations of the common vehicle system.

13. The method of claim 12, further comprising remotely controlling movements of the vehicle systems by communicating the control inputs to the vehicle systems without any operator disposed onboard the vehicle systems during the movements of the vehicle systems.

14. The method of claim 12, wherein the one or more characteristics of the common vehicle system includes an operating state of the common vehicle system, wherein the operating state of the common vehicle system includes one or more of:
the common vehicle system entering into or approaching a particular geographic region of interest, or
the common vehicle system transporting hazardous cargo.

15. The method of claim 12, wherein the control inputs include designated upper limits on movements of the vehicle control systems.

16. The method of claim 12, further comprising:
monitoring a physiological condition of at least one of the remote operators controlling the one or more of the different operations of the common vehicle system; and
determining that the remote operator ratio needs to change based at least in part on the physiological condition of the at least one of the remote operators.

17. The method of claim 16, further comprising monitoring sensor data provided by a sensor array disposed offboard the vehicle systems, the sensor data representative of the physiological condition of the at least one of the remote operators, wherein the sensor data includes one or more of:
images or video of the at least one of the remote operators,
a pulse rate, a respiration rate, a blood pressure, or a movement of the at least one of the remote operators, or
electroencephalogram (EEG) data or electrocardiogram (ECG) data of the at least one of the remote operators.

18. A distributed control system comprising:
a remote control system configured to be communicatively coupled with plural separate vehicle systems, the plural separate vehicle systems mechanically separated from each other, the remote control system configured to remotely control different operations of the vehicle systems, the remote control system configured to assign each of the plural separate vehicle systems to one or more of plural remote operators, the remote control system configured to communicate a first control signal to the vehicle systems to designate an upper speed limit on the movement of one or more of the vehicle systems while allowing one or more of the vehicle systems to move at one or more slower speeds than the upper speed limit of the corresponding vehicle system; and
an alerter system configured to monitor an alertness of a first remote operator of the plural remote operators, the first remote operator configured to remotely control the different operations of a first vehicle system of the vehicle systems, wherein the remote control system is configured to change how many of the plural remote operators of the remote control system concurrently control the first vehicle system of the vehicle systems responsive to determining that the first remote operator is not currently alert.

19. The distributed control system of claim 18, wherein the remote control system is configured to switch remote control of the first vehicle system of the vehicle systems to a different, second remote operator responsive to determining that the first remote operator is not currently alert.

20. The distributed control system of claim 18, wherein the remote control system is configured to communicate different first control signals to one or more of the plural separate vehicle systems representative of different upper speed limits for different locations along one or more routes being traveled by the one or more vehicle systems.

* * * * *